US012780774B2

(12) United States Patent
Williams, Sr.

(10) Patent No.: US 12,780,774 B2
(45) Date of Patent: Nov. 3, 2026

(54) ANTIDEPRESSANT COMPOUNDS, PHARMACEUTICAL COMPOSITIONS, AND METHODS OF TREATING DEPRESSION AND OTHER DISORDERS

(71) Applicant: Miralogx LLC, Tampa, FL (US)

(72) Inventor: Jonnie R. Williams, Sr., Sarasota, FL (US)

(73) Assignee: Miralogx LLC, Tampa, FL (US)

( * ) Notice: Subject to any disclaimer, the term of this patent is extended or adjusted under 35 U.S.C. 154(b) by 0 days.

(21) Appl. No.: 19/327,625

(22) Filed: Sep. 12, 2025

(65) Prior Publication Data

US 2026/0042728 A1 Feb. 12, 2026

Related U.S. Application Data

(63) Continuation-in-part of application No. PCT/US2024/018594, filed on Mar. 6, 2024.

(60) Provisional application No. 63/451,891, filed on Mar. 13, 2023, provisional application No. 63/537,744, filed on Sep. 11, 2023, provisional application No. 63/605,144, filed on Dec. 1, 2023.

(51) Int. Cl.

*C07C 225/20* (2006.01)
*A61K 9/00* (2006.01)
*A61K 9/06* (2006.01)
*A61K 31/135* (2006.01)
*A61K 31/4015* (2006.01)
*C07D 207/14* (2006.01)

(52) U.S. Cl.

CPC .......... *C07C 225/20* (2013.01); *A61K 9/0014* (2013.01); *A61K 9/06* (2013.01); *A61K 31/135* (2013.01); *A61K 31/4015* (2013.01); *C07D 207/14* (2013.01); *C07C 2601/08* (2017.05); *C07C 2601/10* (2017.05)

(58) Field of Classification Search

CPC .............. C07C 225/20; C07C 2601/08; C07C 2601/10; A61K 9/0014; A61K 9/06; A61K 31/135; A61K 31/4015; C07D 207/14

See application file for complete search history.

(56) References Cited

U.S. PATENT DOCUMENTS

| | | | | | |
|---|---|---|---|---|---|
| 5,817,699 | A | * | 10/1998 | Flores | A61K 9/0014 514/647 |
| 11,286,230 | B2 | | 3/2022 | Toupy et al. | |
| 2009/0029947 | A1 | | 1/2009 | Wallace et al. | |
| 2009/0186916 | A1 | | 7/2009 | Hayashibe et al. | |
| 2018/0230120 | A1 | | 8/2018 | Shao et al. | |
| 2021/0171487 | A1 | | 6/2021 | Xue et al. | |

FOREIGN PATENT DOCUMENTS

| | | | | | |
|---|---|---|---|---|---|
| WO | WO-2014143646 | A1 | * | 9/2014 | A61K 31/135 |
| WO | 2018/104729 | A1 | | 6/2018 | |
| WO | WO-2019192602 | A1 | * | 10/2019 | C07C 233/32 |

OTHER PUBLICATIONS

Zarantonello, P et al. Novel analogues of ketamine and phencyclidine as NMDA receptor antagonists. Bioorg. Med. Chem. Lett. 2011, 21, 2059-2063. (Year: 2011).*
Singh, N. S. et al. What is hydroxynorketamine and what can it bring to neurotherapeutics? Expert Rev. Neurother. 2014, 14, 1239-1242. (Year: 2014).*
Ketamine. Drug Enforcement Administration, 2013. (Year: 2013).*
Hill, J. W. et al. Consumer Applications of Chemical Principles: Drugs. J. Chem. Ed. 1985, 62, 328-331. (Year: 1985).*
Aug. 6, 2024—International Search Report—Intl App PCT/US2024/18594.
"Pubchem CID 139573263", Create date: Nov. 2, 2019 (Nov. 2, 2019), entire document especially p. 2, compound listed.

* cited by examiner

*Primary Examiner* — Jeffrey H Murray
*Assistant Examiner* — Kristen W Romero
(74) *Attorney, Agent, or Firm* — KellDann Law PLLC; Paul M. Rivard

(57) ABSTRACT

In some aspects, pharmaceutical compounds are disclosed which may be useful for treating pain, depression and/or associated disorders. In another aspect, a pharmaceutical composition includes an effective amount of the compound(s) and a pharmaceutically acceptable vehicle therefor. In yet another aspect, a method of treating pain, depression or various other disorders involves administering the pharmaceutical composition to an individual in need thereof. In some examples, the pharmaceutical composition is formulated as an ointment for topical administration.

20 Claims, 15 Drawing Sheets

DATA FILE C: \CHEM32\2\DATA\01-2024\016.D
SAMPLE NAME: MIR003-AZ02

| | | | |
|---|---|---|---|
| ACQ. OPERATOR | : SYSTEM | SEQ. LINE : | 4 |
| ACQ. INSTRUMENT | : HPLC_DAD_MS | LOCATION : | P2-C2 |
| INJECTION DATE | : 02/01/2024 14:45:32 | INJ : | 1 |
| | | INJ VOLUME : | 5.000 µl |

METHOD : C: \CHEM32\2\Methods\LB20-40 long.M
LAST CHANGED : 23/11/2023 18:39:46 BY SYSTEM
METHOD INFO : LONG BASIC METHOD
20-40% ACN IN 10mM NH4HCO3, 20MIN
ESI+ ESI-

SAMPLE-RELATED CUSTOM FIELDS:

| NAME | VALUE |
|---|---|

ADDITIONAL INFO : PEAK(S) MANUALLY INTEGRATED

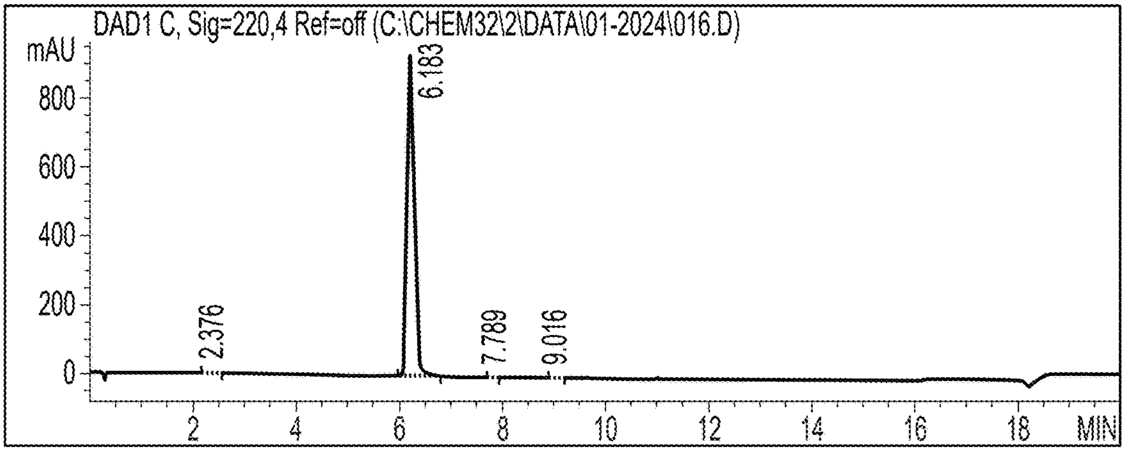

AREA PERCENT REPORT

SORTED BY : SIGNAL
MULTIPLIER : 1.0000
DILUTION : 1.0000
DO NOT USE MULTIPLIER & DILUTION FACTOR WITH ISTDs

SIGNAL 1: DAD1 C, Sig-220,4 Ref-off

| PEAK # | RetTime [MIN] | TYPE | WIDTH [MIN] | AREA [mAU*s] | HEIGHT [mAU] | AREA % |
|---|---|---|---|---|---|---|
| 1 | 2.376 | BB | 0.1352 | 23.91490 | 2.30274 | 0.2695 |
| 2 | 6.183 | BB | 0.1481 | 8831.71777 | 919.22766 | 99.5077 |
| 3 | 7.789 | BB | 0.0986 | 7.76344 | 1.04579 | 0.0875 |
| 4 | 9.016 | BB | 0.1192 | 12.01707 | 1.24651 | 0.1354 |
| TOTALS : | | | | 8875.41319 | 923.82270 | |

FIG. 1

HPLC chromatogram

Data File C:\CHEM32\2\DATA\07-2024\009.D
Sample Name: KIB005-AS040

```
=====================================================================
Acq. Operator   : SYSTEM                         Seq. Line :   2
Acq. Instrument : HPLC_DAD_MS                     Location :   P1-B1
Injection Date  : 01/07/2024 11:50:17                  Inj :   1
                                                Inj Volume : 2.000 µl
Acq. Method     : C:\CHEM32\2\METHODS\L81090.M
Last changed    : 13/11/2023 10:13:13 by SYSTEM
Analysis Method : C:\Chem32\2\Methods\L81090.M
Last changed    : 11/09/2024 11:06:51 by SYSTEM
                  (modified after loading)
Method Info     : Long basic method
                  10-90% ACN in 10mM NH4HCO3, 8min
                  Xbridge C18 50x3.0mm, 3.5um, 1ml/min, 254nm, 215-395nm
                  ESI+


Sample-related custom fields:

Name                             |Value
---------------------------------|-----------------------------------
Additional Info : Peak(s) manually integrated
=====================================================================
```

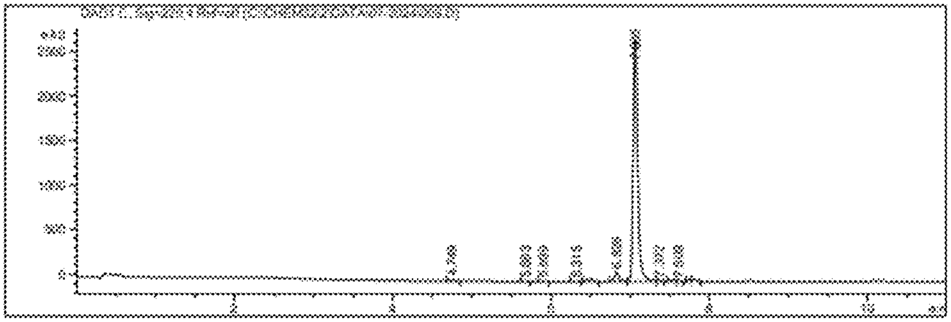

```
=====================================================================
                        Area Percent Report
=====================================================================

Sorted By             :      Signal
Multiplier            :      1.0000
Dilution              :      1.0000
Do not use Multiplier & Dilution Factor with ISTDs


Signal 1: DAD1 C, Sig=220,4 Ref=off
```

| Peak # | RetTime [min] | Type | Width [min] | Area [mAU*s] | Height [mAU] | Area % |
|---|---|---|---|---|---|---|
| 1 | 4.749 | BB | 0.0534 | 27.45165 | 8.13255 | 0.2448 |
| 2 | 5.683 | BB | 0.0462 | 2.06876 | 7.03580e-1 | 0.0184 |
| 3 | 5.899 | BB | 0.0666 | 3.04298 | 7.61105e-1 | 0.0271 |
| 4 | 6.315 | BB | 0.0531 | 5.98137 | 1.69257 | 0.0532 |
| 5 | 6.489 | BB | 0.0551 | 122.09364 | 32.89435 | 1.0876 |
| 6 | 6.828 | BB | 0.0561 | 361.25735 | 100.08828 | 3.2214 |
| 7 | 7.065 | BB | 0.0617 | 1.06188e4 | 2708.67480 | 94.6918 |
| 8 | 7.372 | BB | 0.0494 | 6.86341 | 2.26894 | 0.0612 |
| 9 | 7.529 | BB | 0.0509 | 31.79808 | 10.06454 | 0.2836 |
| 10 | 7.689 | BB | 0.0461 | 1.72085 | 5.89583e-1 | 0.0153 |
| 11 | 7.758 | BB | 0.0404 | 12.10836 | 4.87959 | 0.1080 |
| 12 | 7.819 | BB | 0.0446 | 30.03078 | 10.74545 | 0.2678 |
| Totals : | | | | 1.12141e4 | 2880.78734 | |

*FIG. 8*

Data File C:\CHEM32\2\DATA\07-2024\044.D
Sample Name: MIROOS-AS041 FINAL

Acq. Operator : SYSTEM Seq. Line : 2
Acq. Instrument : HPLC_DAD_MS Location : P1-01
Injection Date : 02/07/2024 17:18:25 Inj : 1
Inj Volume : 2.000 µl
Acq. Method : C:\Chem32\2\Methods\L81090.M
Last changed : 13/11/2023 10:13:13 by SYSTEM
Analysis Method : C:\Chem32\2\Methods\L81090.M
Last changed : 11/09/2024 11:06:51 by SYSTEM
(modified after loading)
Method Info : Long basic method
10-90% ACN in 10mM NH4HCO3, 8min
Xbridge C18 50x3.0mm, 3.5um, 1ml/min, 254nm, 215-395nm
ESI+

Sample-related custom fields:

| Name | Value |
|---|---|
| Additional Info : Peak(s) manually integrated | |

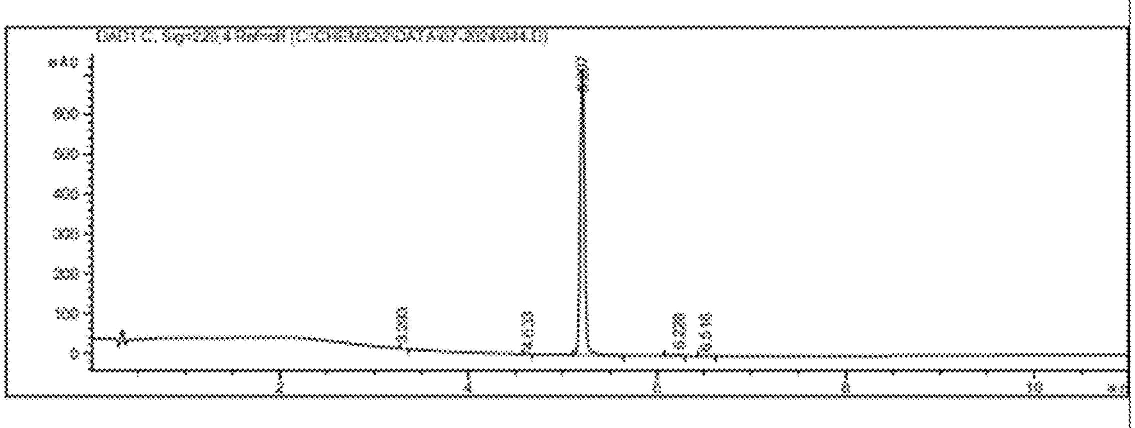

Area Percent Report

Sorted By : Signal
Multiplier : 1.0000
Dilution : 1.0000
Do not use Multiplier & Dilution Factor with ISTDs Signal 1: DAD1 C, Sig=220,4 Ref=off

| Peak # | RetTime [min] | Type | Width [min] | Area [mAU*s] | Height [mAU] | Area % |
|---|---|---|---|---|---|---|
| 1 | 3.293 | BB | 0.0462 | 1.83723 | 6.25993e-1 | 0.0765 |
| 2 | 4.633 | BB | 0.0434 | 3.02894 | 1.12501 | 0.1261 |
| 3 | 5.207 | BB | 0.0524 | 2380.35083 | 723.00073 | 99.0992 |
| 4 | 6.228 | BB | 0.0632 | 13.87795 | 3.29025 | 0.5778 |

*FIG. 9*

```
Data File C:\CHEM32\2\DATA\07-2024\070.D
Sample Name: MIR005-A5042 pr
    =====================================================================
    Acq. Operator   : SYSTEM                         Seq. Line :  10
    Acq. Instrument : HPLC_DAD_MS                     Location :   P1-01
    Injection Date  : 04/07/2024 11:52:11                  Inj :   1
                                                  Inj Volume : 2.000 µl
    Acq. Method     : C:\Chem32\2\Methods\LB1090.M
    Last changed    : 13/11/2023 10:13:13 by SYSTEM
    Analysis Method : C:\Chem32\2\Methods\LB1090.M
    Last changed    : 11/09/2024 11:06:51 by SYSTEM
                      (modified after loading)
    Method Info     : Long basic method
                      10-98% ACN in 10mM NH4HCO3, 8min
                      Xbridge C18 50x3.0mm, 3.5um, 1ml/min, 254nm, 215-395nm
                      ESI+


    Sample-related custom fields:

    Name                          |Value
    ------------------------------|---------------------------------------
    Additional Info : Peak(s) manually integrated
    =====================================================================
```

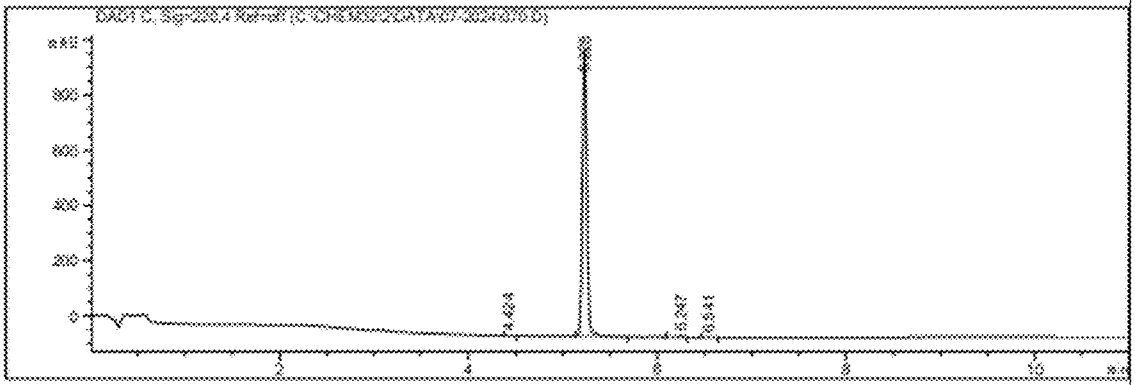

```
    =====================================================================
                        Area Percent Report
    =====================================================================

    Sorted By             :      Signal
    Multiplier            :      1.0000
    Dilution              :      1.0000
    Do not use Multiplier & Dilution Factor with ISTDs


    Signal 1: DAD1 C, Sig=220,4 Ref=off
```

| Peak # | RetTime [min] | Type | Width [min] | Area [mAU*s] | Height [mAU] | Area % |
|---|---|---|---|---|---|---|
| 1 | 4.424 | BB | 0.0532 | 1.92400 | 5.71901e-1 | 0.0553 |
| 2 | 5.228 | BB | 0.0527 | 3460.53076 | 1043.11719 | 99.4247 |
| 3 | 6.247 | BB | 0.0618 | 14.82754 | 3.78068 | 0.4260 |
| 4 | 6.541 | BB | 0.0634 | 3.27076 | 7.42323e-1 | 0.0940 |

FIG. 10

Data File C:\CHEM32\2\DATA\07-2024\119.D
Sample Name: MIR085-AS045

Acq. Operator : SYSTEM    Seq. Line : 4
Acq. Instrument : HPLC_DAD_MS    Location : P1-01
Injection Date : 08/07/2024 12:30:59    Inj : 1
Inj Volume : 2.000 µl Acq. Method : C:\Chem32\2\Methods\LB1090.M
Last changed : 13/11/2023 10:13:13 by SYSTEM
Analysis Method : C:\Chem32\2\Methods\LB1090.M
Last changed : 11/09/2024 11:06:51 by SYSTEM
(modified after loading)
Method Info : Long basic method
10-98% ACN in 10mM NH4HCO3, 8min
Xbridge C18 50x3.0mm, 3.5um, 1ml/min, 254nm, 215-395nm
ESI+

Sample-related custom fields:

| Name | Value |
|---|---|
| Additional Info | Peak(s) manually integrated |

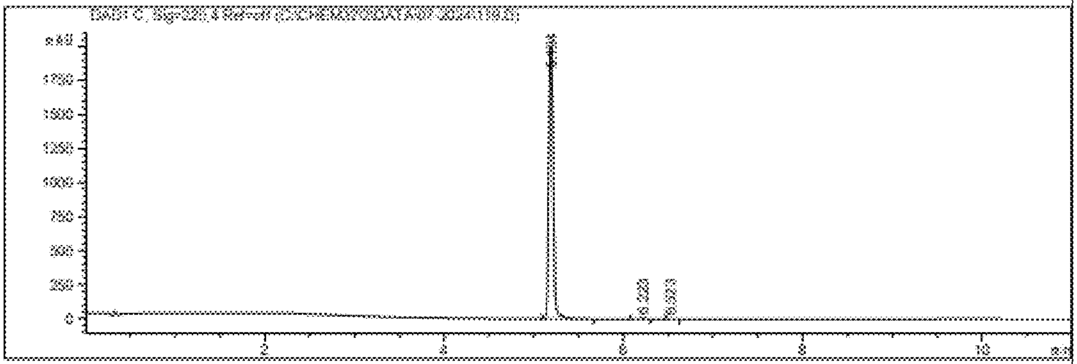

Area Percent Report

Sorted By : Signal
Multiplier : 1.0000
Dilution : 1.0000
Do not use Multiplier & Dilution Factor with ISTDs Signal 1: DAD1 C, Sig=220,4 Ref=off

| Peak # | RetTime [min] | Type | Width [min] | Area [mAU*s] | Height [mAU] | Area % |
|---|---|---|---|---|---|---|
| 1 | 5.194 | BB | 0.0535 | 6819.31934 | 2016.32918 | 99.6114 |
| 2 | 6.223 | BB | 0.0573 | 24.06522 | 6.48858 | 0.3515 |
| 3 | 6.523 | BB | 0.0638 | 2.53863 | 5.71131e-1 | 0.0371 |

FIG. 14

| No. | Peak Name | Retention Time min | Area mAU*min | Height mAU | Rel.Area (GROU % | Relative Height % | Amount |
|---|---|---|---|---|---|---|---|
| n.a. | pomoic imp 1 | n.a. | n.a. | n.a. | n.a. | n.a. | n.a. |
| 1 | Ketamir imp 1 | 10.317 | 0.113 | 1.604 | 0.10 | 0.16 | n.a. |
| n.a. | pomoic imp 3 | n.a. | n.a. | n.a. | n.a. | n.a. | n.a. |
| 2 | Ketamir | 15.693 | 110.326 | 1019.690 | 99.75 | 99.70 | n.a. |
| n.a. | pomoic imp 4 | n.a. | n.a. | n.a. | n.a. | n.a. | n.a. |
| 3 | Ketamir imp 2 | 20.757 | 0.163 | 1.473 | 0.15 | 0.14 | n.a. |
| Total: | | | 110.602 | 1022.768 | 100.00 | 100.00 | |

ANTIDEPRESSANT COMPOUNDS, PHARMACEUTICAL COMPOSITIONS, AND METHODS OF TREATING DEPRESSION AND OTHER DISORDERS

CROSS-REFERENCE TO RELATED APPLICATIONS

This application is a continuation-in-part of International Application No. PCT/US2024/018594, filed Mar. 6, 2024, which claims priority under 35 U.S.C. § 119 (e) to U.S. App. No. 63/451,891, filed Mar. 13, 2023, U.S. App. No. 63/537,744, filed Sep. 11, 2023, and U.S. App. No. 63/605,144, filed Dec. 1, 2023, the disclosures of each of which are hereby incorporated by reference in their entireties.

BACKGROUND

Depression is among the most disabling of all medical disorders with a lifetime prevalence of approximately 17%. It frequently appears early in life, can run a chronic course, and adversely affect the prognosis of other medical illnesses, such as coronary vascular disease, diabetes, and osteoporosis.

Depression is characterized by depressed mood, and markedly diminished interest or pleasure in activities. Other symptoms include significant weight loss or weight gain, decrease or increase in appetite, insomnia or hypersomnia, psychomotor agitation or retardation, fatigue or loss of energy, feelings of worthlessness or excessive or inappropriate guilt, diminished ability to think or concentrate or indecisiveness, recurrent thoughts of death, suicidal ideation or suicidal attempts. A variety of somatic symptoms may also be present. Though depressive feelings are common, especially after experiencing setbacks in life, depressive disorder is diagnosed only when the symptoms reach a threshold and last at least two weeks. Depression can vary in severity from mild to very severe. It is most often episodic but can be recurrent or chronic. Some people have only a single episode, with a full return to premorbid function. However, more than 50 percent of those who initially suffer a single major depressive episode eventually develop another.

Depression is more common in women than in men. The point prevalence of unipolar depressive episodes is estimated to be 1.9% for men and 3.2% for women, and 5.8% of men and 9.5% of women will experience a depressive episode in a 12-month period. These prevalence figures vary across populations and may be higher in some populations. A World Health Organization study has reported that depression is the leading global cause of years of life lived with disability and the fourth leading cause of disability-adjusted life-years. Disability-adjusted life-years refers to the reduction in an individual's productive life, and is a measure that takes into account premature mortality.

The treatment of depression was revolutionized about a half-century ago by the serendipitous discovery of monoamine oxidase inhibitors and tricyclic antidepressants. Since then, the availability of a host of newer medications with better side effect profiles has greatly increased our ability to safely treat a significant percentage of patients. However, the newer medications are largely drugs that merely augment or otherwise potentiate the effects of the existing drugs by exerting their primary biochemical effects by increasing the intrasynaptic levels of monoamines.

Unfortunately, current medications for the treatment of depression take weeks to months to achieve their full effects and in the meantime, patients continue to suffer from their symptoms and continue to be at risk of self-harm as well as harm to their personal and professional lives. Indeed, the lag period of onset of action of several weeks of traditional antidepressants is recognized as a major limitation, resulting in considerable morbidity and high risk of suicidal behavior especially in the first 9 days of starting antidepressants. Pharmacological strategies that have rapid onset of antidepressant effects within hours or a few days and that are sustained would therefore have an enormous impact on public health.

Recently, an "initiation and adaptation" paradigm for understanding the delayed therapeutic actions of antidepressants has been proposed. This paradigm posits that the effect of acute drug administration is mediated via an initial direct target protein perturbation (e.g. binding to a monoamine transporter, thereby resulting in monoamine reuptake inhibition); with repeated administration, the same initial event, over time, leads to enduring adaptive changes in critical neuronal networks, thereby resulting in stable long-term antidepressant effects. Thus, this paradigm posits that the delay in the therapeutic actions of existing pharmacologic agents is due to the fact that they initially act on proteins, which are considerably upstream of the target genes, which are ultimately responsible for the antidepressant effects. In this context, the major systems that have been postulated to mediate the delayed adaptive effects of antidepressants are neurotrophic signaling cascades and the glutamatergic system.

The actions of antidepressants on neurotrophic signaling cascades has been discussed by a number of groups. The context of the present application is with respect to the role of the glutamatergic system, most notably the NMDA system, in the actions of antidepressants. NMDA receptor antagonists have antidepressant effects in many animal models of depression, including the application of inescapable stressors, forced-swim, and tail suspension-induced immobility tests, in learned helplessness models of depression, and in animals exposed to a chronic mild stress procedure. A single dose of the NMDA antagonist ketamine in male Wistar rats interferes with the induction of behavioral despair for up to 10 days after its administration. Additionally, repeated administration of different classes of antidepressants—in a time frame consistent with the delayed therapeutic effects-brings about alterations in the expression of NMDA subunit mRNA and radioligand binding to these receptors in regions of the brain implicated in the pathophysiology of depression.

Several lines of evidence also suggests that dysfunction of the glutamatergic system may play an important role in the pathophysiology of depression. Notably, a recent study by Sanacora et al. showed glutamate levels in the occipital cortex to be significantly elevated, in 29 medication-free subjects with unipolar major depression, as compared to 28 age- and gender-matched healthy controls. Together, these data support the hypothesis of regional alterations in glutamatergic signaling in mood disorders. Finally, in clinical trials, the glutamatergic modulators lamotrigine and riluzole (both inhibitors of glutamate release) were found to have antidepressant properties.

Ketamine has been used in the treatment of breakthrough pain (BTP) in chronic pain patients. In such patients, 10-50 mg of ketamine has been administered through intranasal administration in incremental 10 mg doses, every 90 seconds. The effect of that intranasal administration of ketamine was that there was a lower BTP in patients that received intranasal ketamine as opposed to placebo. There were very few side effects with such administration.

Transdermal administration of ketamine has also been used for the treatment of intractable neuropathic pain. Results indicated that subjects given a dose of 75 mg showed significant improvement in pain disability, and subjective physical and mental function. Azevedo et al. report the results of a randomized, double-blind, placebo-controlled trial using racemic ketamine in a transdermal delivery system after minor abdominal gynecological surgery using lidocaine epidural blockade. At the end of the surgical procedure, a controlled delivery transdermal patch containing either ketamine (25 mg/24 hours) or placebo was applied. The time to rescue analgesic was longer in the ketamine group (230±112 minutes) compared to the placebo group (94±54 minutes).

Ketamine has not been approved for use as an antidepressant, but its enantiomer, esketamine, was developed as a nasal spray for treatment-resistant depression and was approved for this indication in the United States in March 2019. The effectiveness of esketamine is limited, however, with significant effectiveness for treatment-resistant depression seen in only two of five clinical trials. Although there is evidence to support the effectiveness of ketamine and esketamine in treating depression, there is a lack of consensus on dosing and the effects and safety of long-term therapy. Ketamine can produce euphoria and dissociative hallucinogen effects at higher doses, and thus has an abuse potential. Moreover, ketamine has been associated with cognitive deficits, urotoxicity, hepatotoxicity, and other complications in some individuals with long-term use. These undesirable effects may serve to limit the use of ketamine and esketamine for depression.

(R,S)-Ketamine is rapidly metabolized to form a range of metabolites in vivo, including 12 unique hydroxynorketamines (HNKs) that are distinguished by a cyclohexyl ring hydroxylation at the 4, 5, or 6 position and unique stereochemistry at two stereocenters, are formed from the metabolism of ketamine in vivo. See Highland et al., "Hydroxynorketamines: Pharmacology and Potential Therapeutic Applications," *Pharmacological Reviews*, April 2021, 73 (2) 763-791.

There remains a need for improved therapies for treating depression, neuropathic pain, and other disorders such as anxiety, asthma, and seizures. It would be particularly desirable to develop a compound that avoids some or all the above-described drawbacks associate with presently available therapies including ketamine.

SUMMARY

In one aspect, the present disclosure relates to a compound having a structure of Formula (I):

Formula (I)

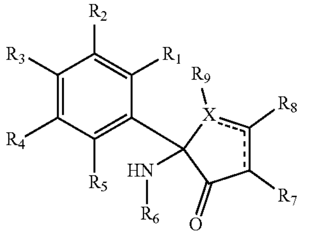

wherein $R_1$, $R_2$, $R_3$, $R_4$, $R_5$, $R_6$, $R_7$, $R_8$, and $R_9$ are each independently selected from the group consisting of an electron pair, H, a halogen, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein ---- is a single bond or a double bond with the proviso that at least one ---- is a single bond; wherein at least one of $R_1$, $R_2$, $R_3$, $R_4$, and $R_5$ is a halogen; and wherein X is C or N; or a pharmaceutically acceptable salt or ester thereof.

In some embodiments, $R_1$ in Formula (I) is a halogen. In some embodiments, the halogen is selected from the group consisting of fluorine (F), chlorine (Cl), bromine (Br), and iodine (I). In some embodiments, the halogen is Cl.

In some embodiments, $R_6$ in Formula (I) is hydrogen. In some embodiments, $R_7$, $R_8$ and/or $R_9$ in Formula (I) is OH.

In some embodiments, both ---- are single bonds. In some embodiments, X in Formula (I) is C. In some embodiments, X in Formula (I) is N.

In another aspect of the present disclosure, a compound has a structure according to Formula (II):

Formula (II)

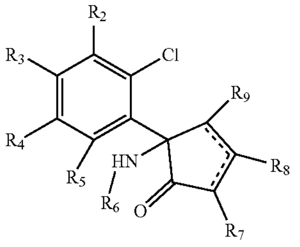

or a pharmaceutically acceptable salt or ester thereof.

In some embodiments, $R_6$ in Formula (II) is hydrogen. In some embodiments, $R_7$, $R_8$ and/or $R_9$ in Formula (II) is OH. In some embodiments, both ---- are single bonds. In other embodiments, one ---- is a single bond and the other ---- is a double bond.

In another aspect, the present disclosure relates to a compound having a structure of Formula (III):

Formula (III)

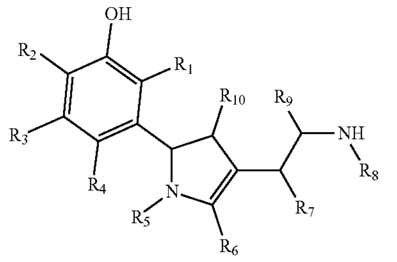

wherein $R_1$, $R_2$, $R_3$, $R_4$, $R_5$, $R_6$, $R_7$, $R_8$, $R_9$, and $R_{10}$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; or a pharmaceutically acceptable salt or ester thereof. In some embodiments, $R_8$ in Formula (III) is hydrogen.

In another aspect, the present disclosure relates to a compound having a structure of Formula (IV):

Formula (IV)

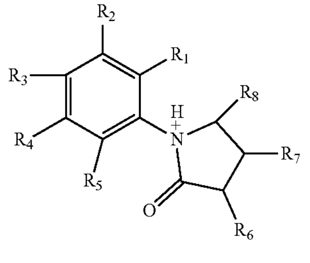

wherein $R_1$, $R_2$, $R_3$, $R_4$, $R_5$, $R_6$, $R_7$, and $R_5$ are each independently selected from the group consisting of an electron pair, H, halogen, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein at least one of $R_1$, $R_2$, $R_3$, $R_4$, and $R_5$ is an halogen, or a pharmaceutically acceptable salt or ester thereof.

In some embodiments, $R_1$ in Formula (IV) is an halogen. In some embodiments, the halogen is selected from the group consisting of fluorine (F), chlorine (CI), bromine (Br), and iodine (I). In some embodiments, the halogen is Cl.

In another aspect, a compound has a structure according to Formula (V):

Formula (V)

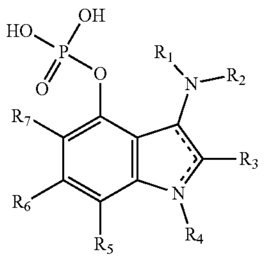

wherein $R_1$, $R_2$, $R_3$, $R_4$, $R_5$, $R_6$, and $R_7$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein ---- is a single bond or a double bond with the proviso that at least one ---- is a single bond; wherein at least one of $R_1$, $R_2$, $R_3$, $R_4$, and $R_5$ is an halogen; and wherein X is C or N; or a pharmaceutically acceptable salt or ester thereof.

In some embodiments, $R_1$ and $R_2$ are each methyl.

In some embodiments, at least one of ---- is a double bond in Formula (V).

In another aspect, a pharmaceutical composition comprises a therapeutically effective amount of a compound having one of the structures depicted above, and a pharmaceutically acceptable vehicle therefor.

In yet another aspect, a method of treating depression, anxiety, asthma, or pain comprises administering to an individual in need thereof a therapeutically effective amount of said pharmaceutical composition.

In still another aspect, a method of inducing anesthesia or sedation comprises administering to an individual in need thereof a therapeutically effective amount of said pharmaceutical composition.

BRIEF DESCRIPTION OF THE DRAWINGS

FIG. 1 shows HPLC analysis of the product 2-(2-chlorophenyl)-2-(methylamino) cyclopentan-1-one hydrochloride.

FIG. 8 shows HPLC analysis of an intermediate ("Int-1") used in the synthesis of 2-(2-chlorophenyl)-2-(methylamino)cyclopentan-1-one pamoate.

FIGS. 9 and 10 shows HPLC analysis of 2-(2-chlorophenyl)-2-(methylamino) cyclopentan-1-one before and after recrystallization, respectively.

FIG. 14 shows HPLC analysis of the intermediate 2-(2-chlorophenyl)-2-(methylamino)cyclopentan-1-one hydrochloride.

DETAILED DESCRIPTION

Figure 2:
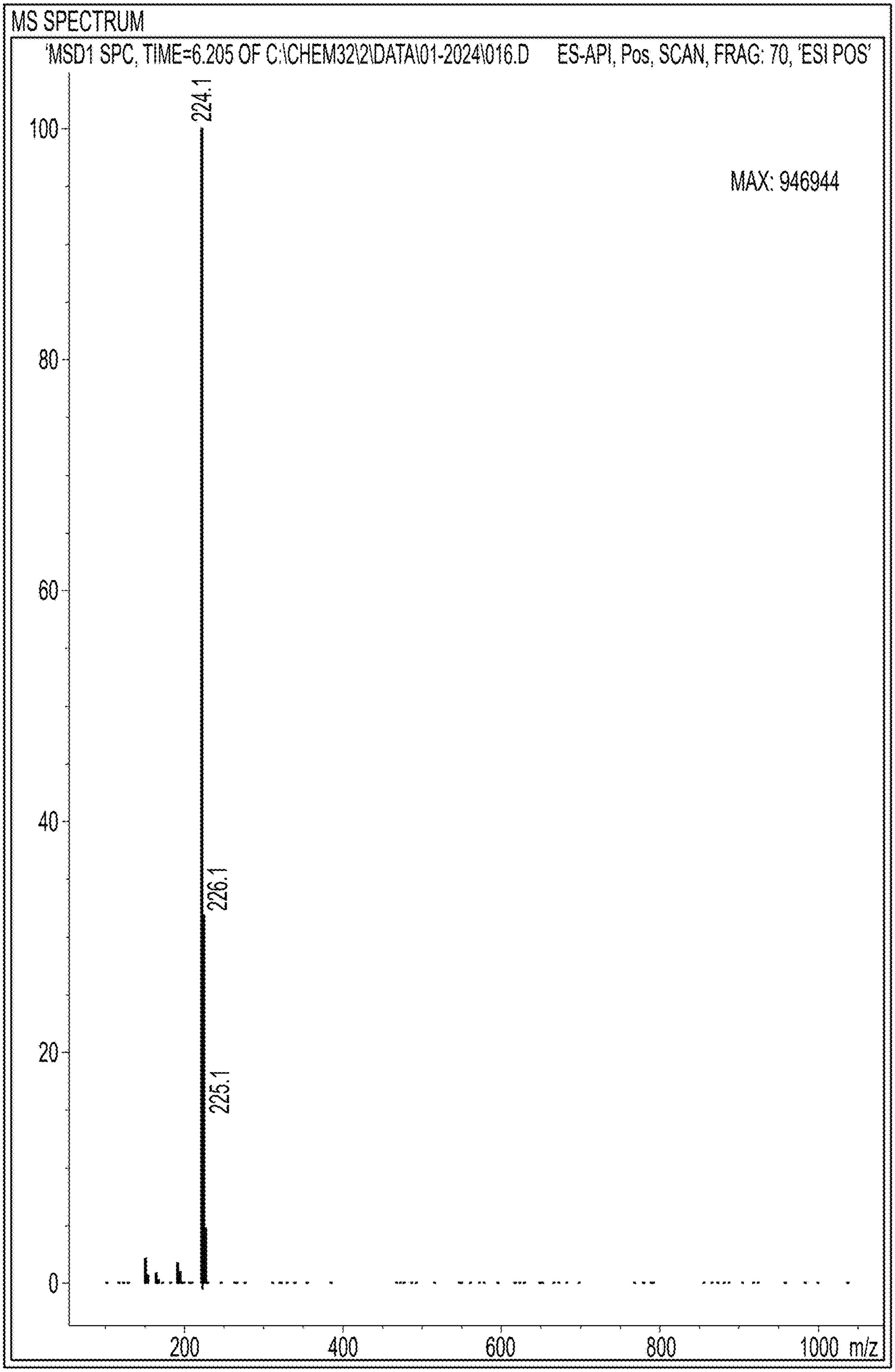
FIG. 2 shows mass spectroscopy analysis of the product 2-(2-chlorophenyl)-2-(methylamino)cyclopentan-1-one hydrochloride.

The present disclosure introduces novel pharmaceutical compounds. In one aspect, the present disclosure relates to a compound having a structure of Formula (I):

Formula (I)

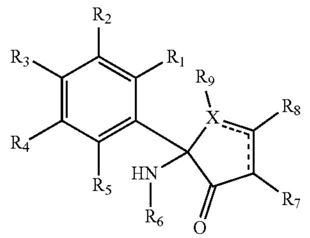

wherein $R_1$, $R_2$, $R_3$, $R_4$, $R_5$, $R_6$, $R_7$, $R_8$, and $R_9$ are each independently selected from the group consisting of an electron pair, H, a halogen, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein ---- is a single bond or a double bond with the proviso that at least one ---- is a single bond; wherein at least one of $R_1$, $R_2$, $R_3$, $R_4$, and $R_5$ is a halogen; and wherein X is C or N; or a pharmaceutically acceptable salt or ester thereof.

In some embodiments, $R_1$ in Formula (I) is a halogen. In some embodiments, the halogen is selected from the group consisting of fluorine (F), chlorine (CI), bromine (Br), and iodine (I). In some embodiments, the halogen is Cl.

In some embodiments, $R_6$ in Formula (I) is a methyl. In some embodiments, $R_6$ in Formula (I) is hydrogen. In some embodiments, $R_6$ in Formula (I) is an ethyl. In some embodiments, $R_6$ in Formula (I) is a $C_{1-4}$ alkyl.

In some embodiments, X in Formula (I) is N. In some embodiments, X in Formula (I) is C.

In some embodiments, both ---- are single bonds.

In another aspect of the present disclosure, a compound has a structure according to Formula (II):

Formula (II)

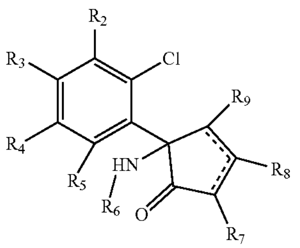

or a pharmaceutically acceptable salt or ester thereof.

In some embodiments, $R_6$ in Formula (II) is hydrogen. In some embodiments, $R_7$, $R_8$ and/or $R_9$ in Formula (II) is OH. In some embodiments, both ---- are single bonds. In other embodiments, one ---- is a single bond and the other ---- is a double bond.

In some embodiments, a compound has a structure selected from the group consisting of:

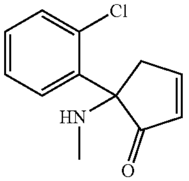

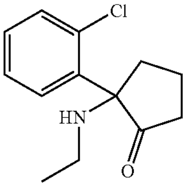

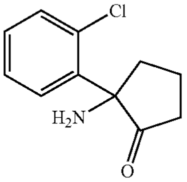

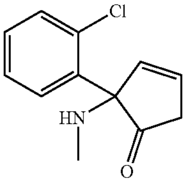

and

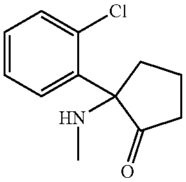

or a pharmaceutically acceptable salt, ester, or ether thereof.

In some embodiments, a compound has a structure selected from the group consisting of:

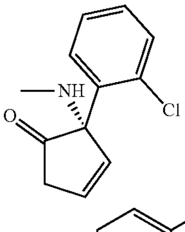

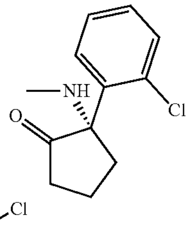

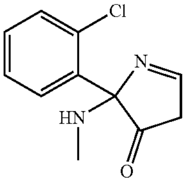

, or a pharmaceutically acceptable salt, ester, or ether thereof.

In another aspect, the present disclosure relates to a compound having a structure of Formula (III):

Formula (III)

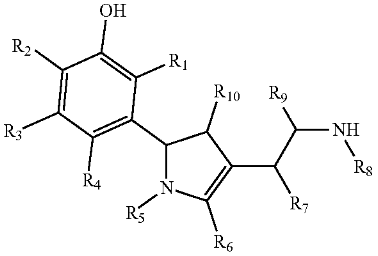

wherein $R_1$, $R_2$, $R_3$, $R_4$, $R_5$, $R_6$, $R_7$, $R_8$, $R_9$, and $R_{10}$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; or a pharmaceutically acceptable salt or ester thereof. In some embodiments, $R_8$ in Formula (III) is hydrogen.

In some embodiments, a compound disclosed herein has the structure:

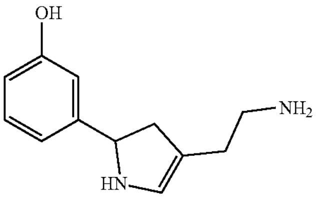 [SMILES: NCCC1=CNC(c2cccc(O)c2)C1]

or a pharmaceutically acceptable salt, ester, or ether thereof.

In another aspect, the present disclosure relates to a compound having a structure of Formula (IV):

Formula (IV)

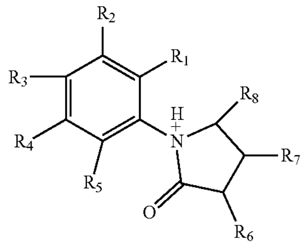

wherein $R_1$, $R_2$, $R_3$, $R_4$, $R_5$, $R_6$, $R_7$, and $R_5$ are each independently selected from the group consisting of an electron pair, H, halogen, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein at least one of $R_1$, $R_2$, $R_3$, $R_4$, and $R_5$ is an halogen, or a pharmaceutically acceptable salt or ester thereof.

In some embodiments, $R_1$ in Formula (IV) is an halogen. In some embodiments, the halogen is selected from the group consisting of fluorine (F), chlorine (CI), bromine (Br), and iodine (I). In some embodiments, the halogen is Cl.

In some embodiments, the compound disclosed herein has the structure:

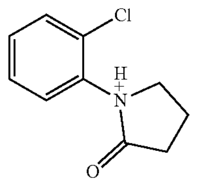

or a pharmaceutically acceptable salt, ester, or ether thereof.

In another aspect, the compound has a structure according to Formula (V):

Formula (V)

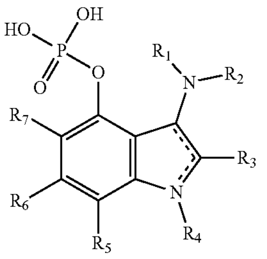

wherein $R_1$, $R_2$, $R_3$, $R_4$, $R_5$, $R_6$, and $R_7$ are each independently selected from the group consisting of an electron pair, H, OH, protected hydroxyl, alkyl, alkenyl, alkynyl, acyl, aryl, heteroaryl, cycloalkyl, phenyl, carbonate ester, a carboxylate, a carboxyl, an ester, a hydroperoxy, a peroxy, an ether, a hemiacetal, a hemiketal, an acetal, a ketal, an orthoester, a methylenedioxy, an orthocarbonate ester, carboxamide, an amine, an imine, an amide, an azide, an azo, a cyanate, a nitrate, a nitrile, an isonitrile, a nitrosooxy, a nitro, a pyridyl, a thiol, a sulfide, sulfinyl, a sulfonyl, a thiocyanate, a carbonothioyl, a phosphate, and heterocycle; optionally wherein the alkyl, alkenyl, alkynyl or acyl is substituted with one or more substituents independently selected from the group consisting of halogen, —OH, alkyl, —O-alkyl, $NR^AR^B$, —S-alkyl, —SO-alkyl, —$SO_2$-alkyl, alkenyl, alkynyl, aryl, heteroaryl, cycloalkyl, and heterocycle; wherein $R^A$ and $R^B$ are each independently selected from hydrogen and $C_{1-4}$ alkyl; wherein the aryl or heteroaryl, whether alone or as part of a substituent group, is optionally substituted with one or more substituents independently selected from the group consisting of halogen, —OH, alkyl, —O-alkyl, —COOH, —C(O)—$C_{1-4}$ alkyl, —C(O)O—$C_{1-4}$ alkyl, $NR^CR^D$, —S-alkyl, —SO-alkyl and —$SO_2$-alkyl; wherein $R^C$ and $R^D$ are each independently selected from hydrogen and $C_{1-4}$ alkyl; wherein ---- is a single bond or a double bond with the proviso that at least one ---- is a single bond; wherein at least one of $R_1$, $R_2$, $R_3$, $R_4$, and $R_5$ is an halogen; and wherein X is C or N; or a pharmaceutically acceptable salt or ester thereof.

In some embodiments, $R_1$ and $R_2$ are each methyl.

In some embodiments, at least one of ---- is a double bond in Formula (V).

In some embodiments, the compound is

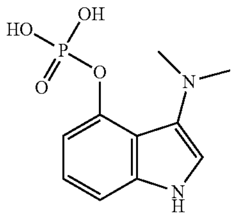 [SMILES: CN(C)c1c[nH]c2cccc(OP(=O)(O)O)c12]

or a pharmaceutically acceptable salt or ester thereof.

In other aspects of the present disclosure, a compound has a structure selected from the group consisting of:

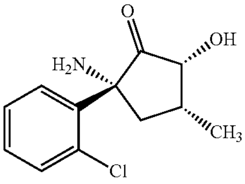
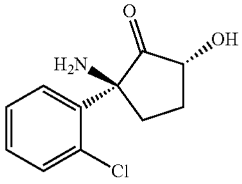
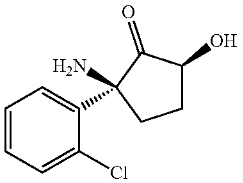
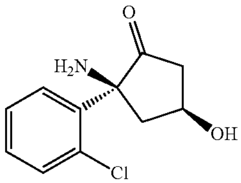
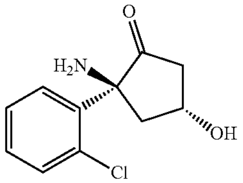
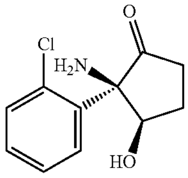
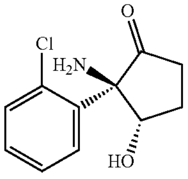
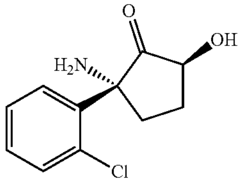
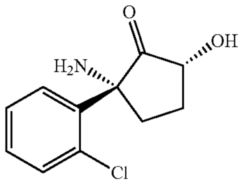
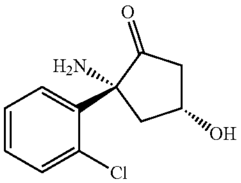
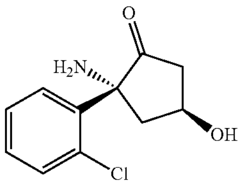
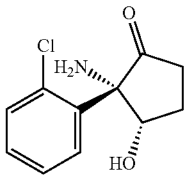
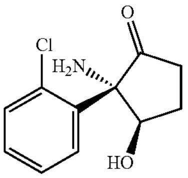
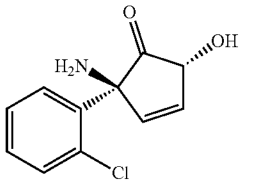
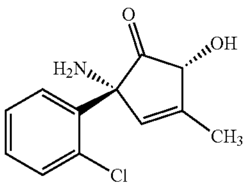
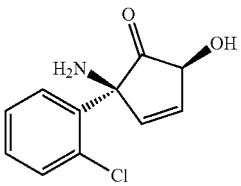
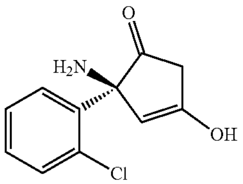
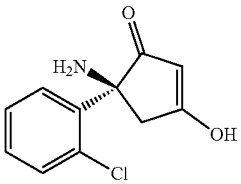

-continued

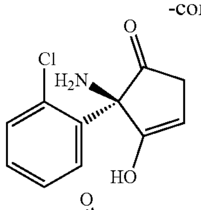
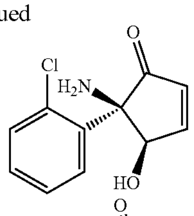
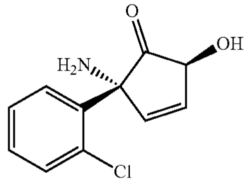
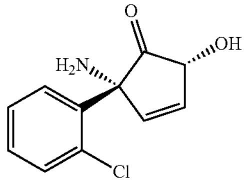
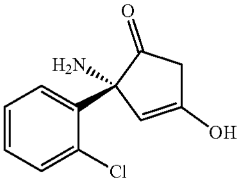
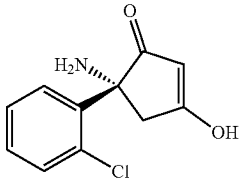
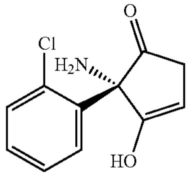
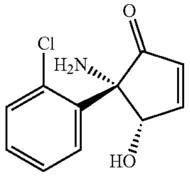
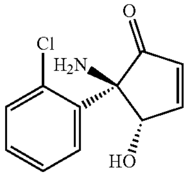
and
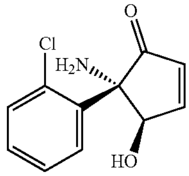, or a pharmaceutically acceptable salt, ester, or ether thereof.

Synthesis of Compounds

In some examples, compounds may be prepared synthetically using techniques described in C. Chen et al., "Enantioselective Syntheses of(S)-Ketamine and(S)-Norketamine," Org. Lett. 2019, 21, 16, 6575-6578 (2019) (available at doi.org/10.1021/acs.orglett.9b02575), with appropriate modifications of reagents to obtain the structures described herein as will be apparent to persons skilled in the art. In some examples, the compounds may be synthesized based on techniques described in Zhang et al., Org. Lett. 2017, 19, 1124, which describes a short synthesis of ketamine via direct nitration of cyclic ketones, followed by selective reduction of nitro functionality to afford a primary amine, which is subsequently monomethylated by reductive amination. In some examples, the compounds described herein may be synthesized based on techniques described in J. Highland et al., "Hydroxynorketamine Pharmacokinetics and Antidepressant Behavioral Effects of (2,6)- and (5R)-Methyl-(2R,6R)-hydroxynorketamines," ACS Chem. Neurosci. 2022, 13, 4, 510-523. Yet another approach is described in Stevens et al., J. Org. Chem. 1965, 30, 2962, which enables a short synthesis of ketamine via an α-bromination of the starting material, followed by a one-step formation of α-hydroxyl and shiff-base intermediate, which is subsequently undergoing a rearrangement to provide the required product. Bromination of an α-position of the starting material 2-(2-chlorophenyl) cyclopentanone may be followed by a substitution with methyl hydroxylamine and reduction of the obtained intermediate. As an alternative, the brominated intermediate may be exposed directly to methylamine to provide the required product.

In some aspects, the compounds may be converted into a pharmaceutically acceptable salts using techniques well known to persons skilled in the art. For example, salts such as sodium and potassium salts may be prepared by treating the compound with a suitable sodium or potassium base, such as sodium hydroxide or potassium hydroxide, respectively. Esters and ethers of the compounds may be prepared as described, e.g., in Advanced Organic Chemistry, 1992, 4th Edition, J. March, John Wiley & Sons, or J. Med. Chemistry, 1992, 35, 145-151.

Pharmaceutical Compositions and Methods of Use

The compounds as described herein are particularly useful for treating depression, and also may be useful for treating a variety of other disorders and indications including anxiety, asthma, anesthesia/sedation, pain, and seizures.

A pharmaceutical composition may include a pharmaceutically acceptable carrier that facilitates processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle," "stabilizer," "diluent," "additive," "auxiliary" or "excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

Compounds intended for administration to humans or other mammals generally should have very high purity. Purity refers to the ratio of a compound's mass to the total sample mass following any purification steps. Usually, the level of purity is at least about 95%, more usually at least about 96%, about 97%, about 98%, or higher. For example, the level of purity may be about 98.5%, 99.0%, 99.1%, 99.2%, 99.3%, 99.4%, 99.5%, 99.6%, 99.7%, 99.8%, 99.9%, or higher.

The compounds described herein that exist in more than one optical isomer form (enantiomer) may be provided either as racemic mixture or by isolating one of the enantiomers, the latter case in which purity as described above may refer to enantiomeric purity.

Compositions as described herein may be administered orally, nasally, topically, subcutaneously, intramuscularly, intravenously, or by other modes of administration. For example, an antidepressant may be formulated as an intranasal spray as described in U.S. Pat. No. 8,785,500 B2, the disclosure of which is hereby incorporated by reference. In some examples, the composition may be formulated as an ointment for topical administration.

A pharmaceutical composition may optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

Examples of auxiliaries and/or excipients that may be mentioned are cremophor, poloxamer, benzalkonium chloride, sodium lauryl sulfate, dextrose, glycerin, magnesium stearate, polyethylene glycol, starch, dextrin, lactose, cellulose, carboxymethylcellulose sodium, talc, agar-agar, mineral oil, animal oil, vegetable oil, organic and mineral waxes, paraffin, gels, propylene glycol, benzyl alcohol, dimethylacetamide, ethanol, polyglycols, tween 80, solutol HS 15, and water. It is also possible to administer the active substances as such, without vehicles or diluents, in a suitable form, for example, in capsules.

A pharmaceutical composition may comprise a therapeutic compound in an amount sufficient to allow customary administration to an individual. A unit dose form may have, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In other aspects, a unit dose form may have, e.g., at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may include, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg of a therapeutic compound. In still other aspects of this embodiment, a pharmaceutical composition disclosed herein may include, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg of a therapeutic compound.

Pharmaceutical compositions as described herein may include a pharmaceutically acceptable solvent. A solvent is a liquid, solid, or gas that dissolves another solid, liquid, or gaseous (the solute), resulting in a solution. Solvents useful in the pharmaceutical compositions include, without limitation, a pharmaceutically acceptable polar aprotic solvent, a pharmaceutically acceptable polar protic solvent and a pharmaceutically acceptable non-polar solvent. A pharmaceutically acceptable polar aprotic solvent includes, without limitation, dichloromethane (DCM), tetrahydrofuran (THF), ethyl acetate, acetone, dimethylformamide (DMF), acetonitrile (MeCN), dimethyl sulfoxide (DMSO). A pharmaceutically acceptable polar protic solvent includes, without limitation, acetic acid, formic acid, ethanol, n-butanol, 1-butanol, 2-butanol, isobutanol, sec-butanol, tert-butanol, n-propanol, isopropanol, 1,2 propan-diol, methanol, glycerol, and water. A pharmaceutically acceptable non-polar solvent includes, without limitation, pentane, cyclopentane, hexane, cyclohexane, benzene, toluene, 1,4-dioxane, chloroform, n-methyl-pyrrolidone (NMP), and diethyl ether.

The method of administration as well as the dosage range which are suitable in a specific case depend on the species to be treated and on the state of the respective condition or disease, and may be optimized using techniques known in the art. Most often, the daily dose of active compound in a patient is 0.0005 mg to 15 mg per kg, more usually 0.001 mg to 7.5 mg per kg. Dosing can be single dosage or cumulative (serial dosing), and can be readily determined by one skilled in the art. For instance, treatment of a bacterial infection may comprise a one-time administration of an effective dose of a pharmaceutical composition as disclosed herein. Alternatively, treatment may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Pharmaceutical compositions may contain any conventional non-toxic pharmaceutically-acceptable carriers, adjuvants or vehicles. In some cases, the pH of the formulation may be adjusted with acceptable pharmaceutical or food grade acids, bases or buffers to enhance the stability of the formulated composition or its delivery form.

Liquid dosage forms for oral administration include acceptable pharmaceutical or food grade emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylsulfoxide (DMSO) dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, lozenges, pills, powders, and granules. In such solid dosage forms, the active compound is mixed with at least one inert, acceptable pharmaceutical or food grade excipient or carrier such as sodium citrate or dicalcium phosphate and/or a) fillers or extenders such as starches, lactose, sucrose, glucose, mannitol, and silicic acid, b) binders such as carboxymethylcellulose, alginates, gelatin, polyvinylpyrrolidone, sucrose and acacia, c) humectants such as glycerol, d) disintegrating agents such as agaragar, calcium carbonate, potato or tapioca starch, alginic acid, certain silicates, and sodium carbonate, e) solution retarding agents such as paraffin, f) absorption accelerators such as quaternary ammonium compounds, g) wetting agents such as cetyl alcohol and glycerol monostearate, h) absorbents such as kaolin and bentonite clay, i) lubricants such as talc, calcium stearate, magnesium stearate, solid polyethylene glycols, sodium lauryl sulfate, and mixtures thereof, and j) sweetening, flavoring, perfuming agents, and mixtures thereof. In the case of capsules, lozenges, tablets and pills, the dosage form may also comprise buffering agents.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract or, optionally, in a delayed or extended manner. Examples of embedding compositions which can be used include polymeric substances and waxes. Tablet formulations for extended release are also described in U.S. Pat. No. 5,942,244.

Compositions may contain a compound as disclosed herein, alone or with other therapeutic compound(s). A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g., a hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. In some aspects, the therapeutic compound may have anti-inflammatory activity, such as a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, aceclofenac, acemetacin, actarit, alcofenac, alminoprofen, amfenac, aloxipirin, aminophenazone, antraphenine, aspirin, azapropazone, benorilate, benoxaprofen, benzydamine, butibufen, celecoxib, chlorthenoxacin, choline salicylate, clometacin, dexketoprofen, diclofenac, diflunisal, emorfazone, epirizole; etodolac, etoricoxib, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, lumiracoxib, mefenamic acid, meloxicam, metamizole, metiazinic acid, mofebutazone, mofezolac, nabumetone, naproxen, nifenazone, niflumic acid, oxametacin, phenacetin, pipebuzone, pranoprofen, propyphenazone, proquazone, protizinic acid, rofecoxib, salicylamide, salsalate, sulindac, suprofen, tiaramide, tinoridine, tolfenamic acid, valdecoxib, and zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclooxygenase (COX) inhibitor, a selective cyclooxygenase-1 (COX-1) inhibitor, and a selective cyclooxygenase-2 (COX-2) inhibitor. An NSAID may be a profen. Examples of a suitable salicylate derivative NSAID include, without limitation, acetylsalicylic acid (aspirin), diflunisal, and salsalate. Examples of a suitable p-amino phenol derivative NSAID include, without limitation, paracetamol and phenacetin. Examples of a suitable propionic acid derivative NSAID include, without limitation, alminoprofen, benoxaprofen, dexketoprofen, fenoprofen, flurbiprofen, ibuprofen, indoprofen, ketoprofen, loxoprofen, naproxen, oxaprozin, pranoprofen, and suprofen. Examples of a suitable acetic acid derivative NSAID include, without limitation, aceclofenac, acemetacin, actarit, alcofenac, amfenac, clometacin, diclofenac, etodolac, felbinac, fenclofenac, indometacin, ketorolac, metiazinic acid, mofezolac, nabumetone, naproxen, oxametacin, sulindac, and zomepirac. Examples of a suitable enolic acid (oxicam) derivative NSAID include, without limitation, droxicam, isoxicam, lornoxicam, meloxicam, piroxicam, and tenoxicam. Examples of a suitable fenamic acid derivative NSAID include, without limitation, flufenamic acid, mefenamic acid, meclofenamic acid, and tolfenamic acid. Examples of a suitable selective COX-2 inhibitors include, without limitation, celecoxib, etoricoxib, firocoxib, lumiracoxib, meloxicam, parecoxib, rofecoxib, and valdecoxib.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Example 1

This example illustrates the synthesis of 2-(2-chlorophenyl)-2-(methylamino) cyclopentan-1-one hydrochloride.

M209•HCl

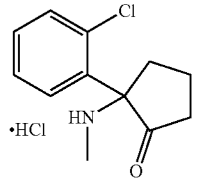

The synthesis, based on Zhang et al (*Org. Lett.* 2017, 19, 1124), involved direct nitration of cyclic ketones, followed by selective reduction of nitro functionality to afford a primary amine, which was subsequently monomethylated by reductive amination and converted to the hydrochloride salt.

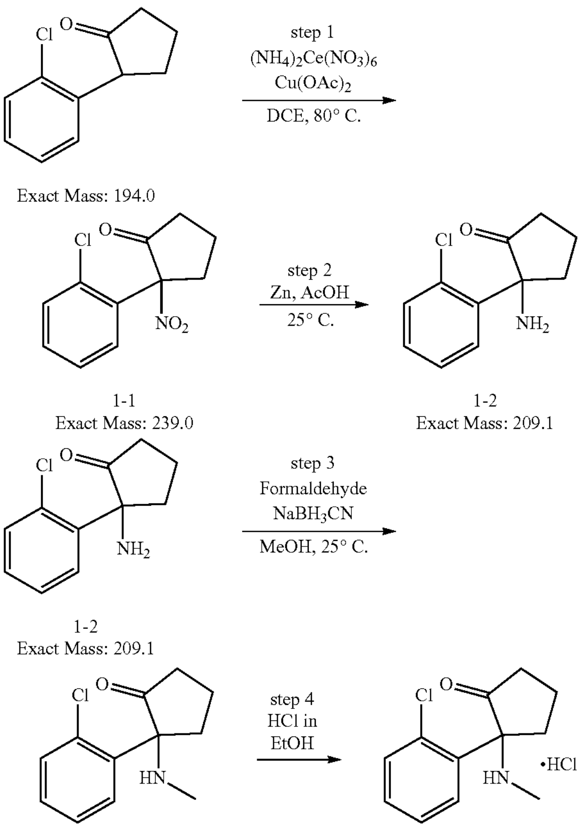

Exact Mass: 194.0
1-1
Exact Mass: 239.0
1-2
Exact Mass: 209.1
1-2
Exact Mass: 209.1

M209
Exact Mass: 223.1

M209•HCl

Nitration of 2-(2-chlorophenyl)cyclopentan-1-one (Int-1-1)

Cerium ammonium nitrate (CAN) was thoroughly dried in a vacuum oven (100° C., 60 mbar). A 350 mL pressure vessel was charged with CAN (71 g, 130 mmol, 2 eq), degassed solution of the ketone (12 g, 62 mmol, 1 eq) in DCE (150 mL) and $Cu(OAc)_2$ (2.25 g, 12 mmol, 0.2 eq). The reaction mixture was stirred at 90° C. under an argon atmosphere for 18 hours. The reaction mixture was poured into DCM (250 mL) and the solution was stirred for 30 min. The reaction mixture was filtered through a Celite pad. The filtrate was washed with a mixture of water/sat. $NaHCO_3$ (50/50), the phases were separated, and the aqueous fraction was extracted with DCM (100 mL). The combined organic fraction was washed with water (100 mL), brine (2×100 mL), dried over $MgSO_4$, filtered, and evaporated. The obtained product was used in the next step without purification (13.9 g).

Reduction of Nitro-Ketone (Int-1-2)

A crude nitroketone 1-1 (13.9 g) from the previous step was dissolved in AcOH (200 mL) in 1 L flask and the flask was put into a water bath at room temperature. Four portions of zinc dust (4×4 g) were added to the reaction mixture every 15 minutes then, after 2 hours, an additional portion of zinc dust (4 g) was added to the reaction mixture. The reaction mixture was quenched when the starting material (nitroketone 1-1, [M+H]+=257) and the intermediate (nitrosoketone, [M+H]+=226) were fully consumed. The reaction mixture was filtered through a Celite pad and evaporated. Water (500 mL) and EtOAc (100 mL) were added to the obtained residue, stirred, and separated. The water fraction was washed with EtOAc (100 mL), and the combined organic fraction I was washed with water (50 mL). The combined water fraction was neutralized with solid $NaHCO_3$ (20 g) and extracted with DCM (3×150 mL) (organic fraction II), yielding a vast amount of stable emulsion. The organic fraction II was dried over $MgSO_4$, filtered, and evaporated (2.9 g product). According to LC-MS the organic fraction I comprised a vast amount of the desired product, thus the organic fraction I was evaporated and dissolved in the mixture of DCM (100 mL), water (250 mL), and 37% f HCl (5 mL). The water fraction was separated, neutralized with solid $NaHCO_3$ (20 g), and extracted with DCM (3×150 mL). The organic phase was separated, dried over $MgSO_4$, filtered, and evaporated (1.3 g product). Overall mass 4.2 g (33% yield (step 1+step 2)).

Monomethylation of Aminoketone (M209)

Formaldehyde (154 mg, 0.7 eq, 0.4 mL of 37% w/w solution in water) was added to the solution of aminoketone 1-2 (1.45 g, 7 mmol, 1 eq) in MeOH (20 mL). In a separate vial, a solution of $NaCNBH_3$ (0.37 g, 5.9 mmol, 0.85 eq) in MeOH (15 mL) was prepared. To the stirred mixture AcOH (0.4 mL, 7 mmol, 1 eq) was added, then after 1.5 min the formaldehyde/aminoketone solution from the previous step was added at room temperature. After 6 minutes the reaction was quenched with water (25 mL). The solution was partially evaporated, and dissolved in $Et_2O$ (200 mL) and water (50 mL), and a water-$Et_2O$ workup was performed. Weight of the crude mixture 1.2 g (77%). The batch was combined with other similar batches and purified by reverse-phase column chromatography. The ACN fraction was evaporated and the product was extracted with DCM, and EtOAC. The organic phases were combined, dried over $Na_2SO_4$, and evaporated. An off-white solid was obtained (~0.8 g, 99% HPLC purity). The tentative yield of all the processes was ~8%.

Formation of M209·HCl

Figure 3:
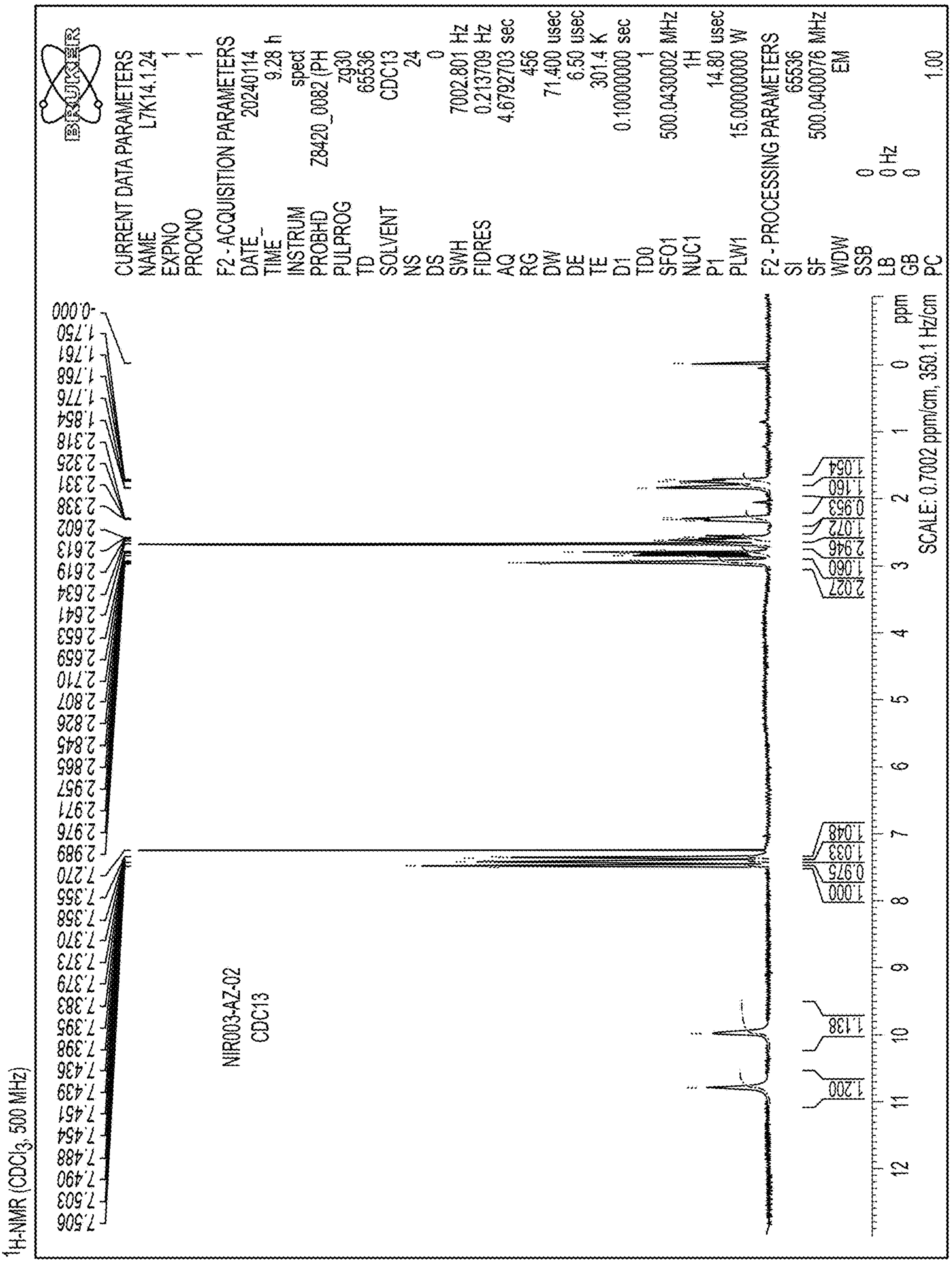
FIG. 3 shows 1H-NMR analysis of the product 2-(2-chlorophenyl)-2-(methylamino) cyclopentan-1-one hydrochloride.
Figure 4:
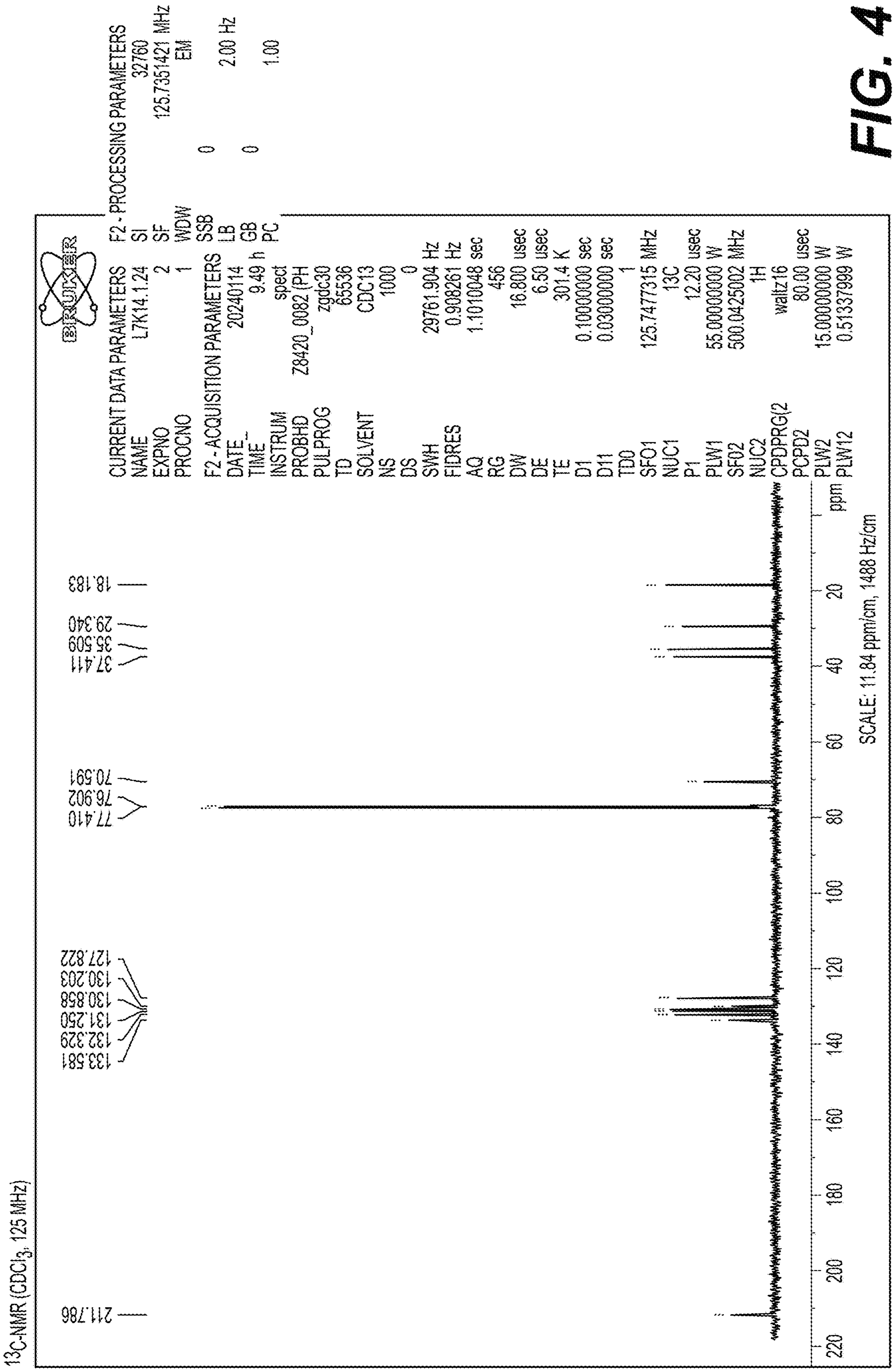
FIG. 4 shows 13C-NMR analysis of the product 2-(2-chlorophenyl)-2-(methylamino) cyclopentan-1-one hydrochloride.
Figure 5:
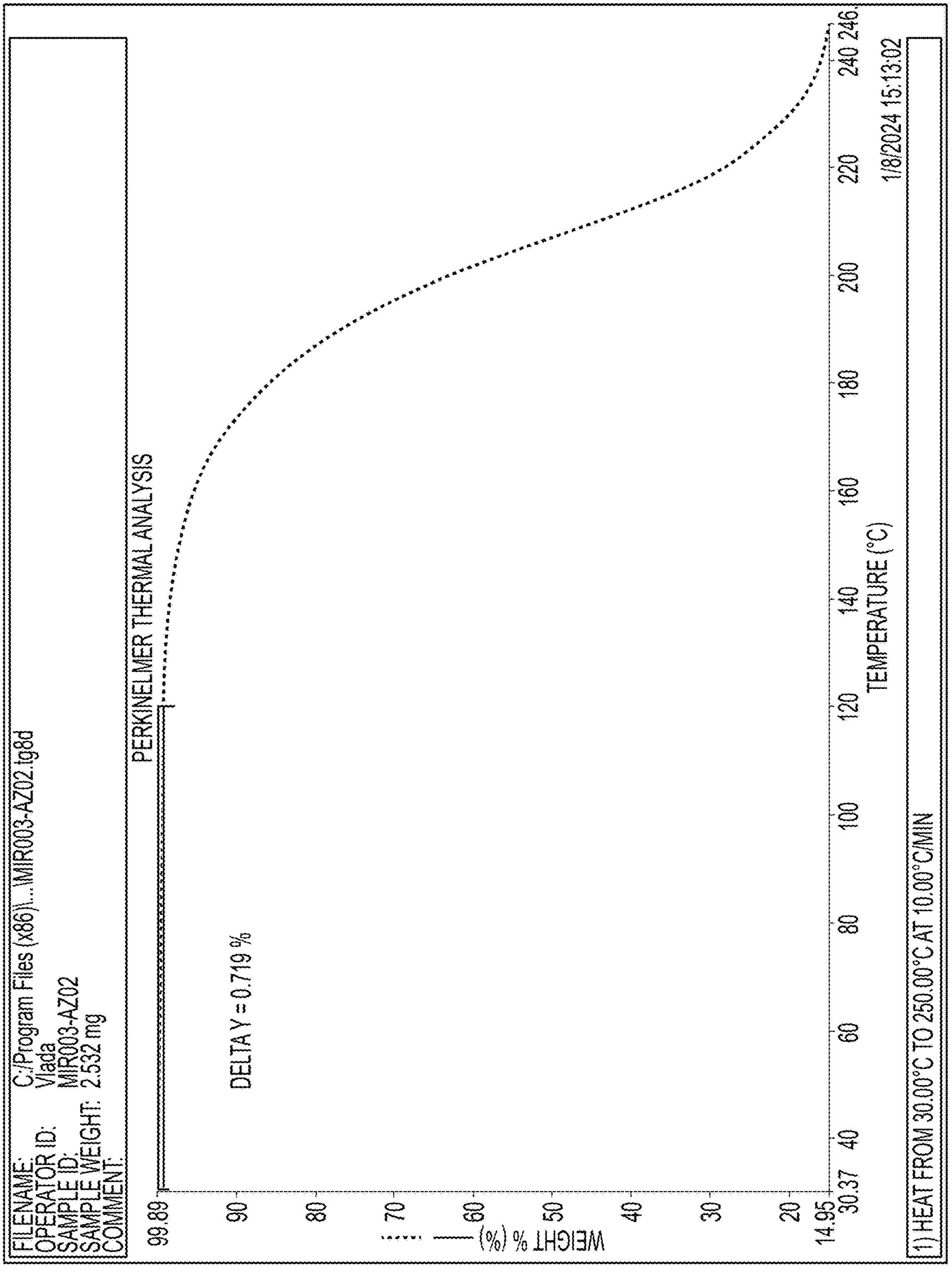
FIG. 5 shows thermogravimetric (TGA) analysis of the product 2-(2-chlorophenyl)-2-(methylamino)cyclopentan-1-one hydrochloride.

The previously isolated M209 was dissolved in EtOH (5-7 mL) and HCl in EtOH (3 mL) was added, the solution was stirred for 5 minutes and evaporated to provide a yellowish oil. Then, a crystallization with $CHCl_3$/heptane was performed, a turbid solution was evaporated to dryness, and an off-white solid was obtained, which was dried on high-vac (0.8 gr, 99.4% HPLC purity). FIG. 1 shows the results of analysis by HPLC. FIG. 2 shows the results of analysis by mass spectroscopy. FIG. 3 and FIG. 4 show the results of analysis by 1H-NMR and 13C-NMR, respectively. FIG. 5 shows the results of thermogravimetric analysis (TGA).

Example 2

This example illustrates evaluating 2-(2-chlorophenyl)-2-(methylamino) cyclopentan-1-one in a panel of cell lines developed by DiscoverX for stably expressing non-tagged GPCRs that signal through cAMP. Hit Hunter® cAMP assays monitor the activation of a GPCR via Gi and Gs secondary messenger signaling in a homogenous, non-imaging assay format using a technology developed by DiscoverX called Enzyme Fragment Complementation (EFC) with β-galactosidase (β-Gal) as the functional reporter.

The enzyme is split into two complementary portions: EA for Enzyme Acceptor and ED for Enzyme Donor. ED is fused to CAMP and in the assay competes with cAMP generated by cells for binding to a cAMP-specific antibody. Active β-Gal is formed by complementation of exogenous EA to any unbound EDCAMP. Active enzyme can then convert a chemiluminescent substrate, generating an output signal detectable on a standard microplate reader.

The Calcium No Wash PLUS assay monitors the activation of a GPCR via Gq secondary messenger signaling in a live cell, nonimaging assay format. Calcium mobilization in PathHunter® cell lines or other cell lines stably expressing Gq-coupled GPCRs is monitored using a calcium-sensitive dye that is loaded into cells. GPCR activation by a compound results in the release of calcium from intracellular stores and an increase in dye fluorescence that is measured in real-time.

Cell Handling

1. CAMP Hunter cell lines were expanded from freezer stocks according to standard procedures.
2. Cells were seeded in a total volume of 20 μL into white walled, 384-well microplates and incubated at 37° C. for the appropriate time prior to testing.
3. cAMP modulation was determined using the DiscoverX HitHunter CAMP XS+ assay.

Gs Agonist Format

1. For agonist determination, cells were incubated with sample to induce response.
2. Media was aspirated from cells and replaced with 15 μL 2:1 HBSS/10 mM Hepes: cAMP XS+Ab reagent.
3. Intermediate dilution of sample stocks was performed to generate 4× sample in assay buffer.
4. 5 μL of 4× sample was added to cells and incubated at 37° C. or room temperature for 30 or 60 minutes. Vehicle concentration was 1%.

Gi Agonist Format

1. For agonist determination, cells were incubated with sample in the presence of EC80 forskolin to induce response.
2. Media was aspirated from cells and replaced with 15 μL 2:1 HBSS/10 mM Hepes: CAMP XS+Ab reagent.
3. Intermediate dilution of sample stocks was performed to generate 4× sample in assay buffer containing 4× EC80 forskolin.
4. 5 μL of 4× sample was added to cells and incubated at 37° C. or room temperature for 30 or 60 minutes. Final assay vehicle concentration was 1%.

Allosteric Modulation Format

1. For allosteric determination, cells were pre-incubated with sample followed by agonist induction at the EC20 concentration.
2. Media was aspirated from cells and replaced with 10 μL 1:1 HBSS/10 mM Hepes: cAMP XS+Ab reagent.
3. Intermediate dilution of sample stocks was performed to generate 4× sample in assay buffer.
4. 5 μL of 4× compound was added to the cells and incubated at room temperature or 37° C. for 30 minutes.
5. 5 μL of 4× EC20 agonist was added to the cells and incubated at room temperature or 37° C. for 30 or 60 minutes. For Gi-coupled GPCRs, EC80 forskolin was included.

Inverse Agonist Format (Gi only)

1. For inverse agonist determination, cells were pre-incubated with sample in the presence of EC20 forskolin.
2. Media was aspirated from cells and replaced with 15 μL 2:1 HBSS/10 mM Hepes: cAMP XS+Ab reagent.
3. Intermediate dilution of sample stocks was performed to generate 4× sample in assay buffer containing 4× EC20 forskolin.
4. 5 μL of 4× sample was added to cells and incubated at 37° C. or room temperature for 30 or 60 minutes. Final assay vehicle concentration was 1%.

Antagonist Format

1. For antagonist determination, cells were pre-incubated with sample followed by agonist challenge at the EC80 concentration.
2. Media was aspirated from cells and replaced with 10 μL 1:1 HBSS/Hepes: CAMP XS+Ab reagent.
3. 5 μL of 4× compound was added to the cells and incubated at 37° C. or room temperature for 30 minutes.
4. 5 μL of 4× EC80 agonist was added to cells and incubated at 37° C. or room temperature for 30 or 60 minutes. For Gi coupled GPCRs, EC80 forksolin was included.

Signal Detection

1. After appropriate compound incubation, assay signal was generated through incubation with 20 μL cAMP XS+ED/CL lysis cocktail for one hour followed by incubation with 20 μL cAMP XS+EA reagent for three hours at room temperature.
2. Microplates were read following signal generation with a PerkinElmer Envision™ instrument for chemiluminescent signal detection.

Data Analysis

1. Compound activity was analyzed using CBIS data analysis suite (ChemInnovation, CA).
2. For Gs agonist mode assays, percentage activity is calculated using the following formula:

$$\%\ \text{Activity} = 100\% \times (\text{mean } RLU \text{ of test sample} - \text{mean } RLU \text{ of vehicle control}) / (\text{mean } RLU \text{ of MAX control} - \text{mean } RLU \text{ of vehicle control}).$$

3. For Gs positive allosteric mode assays, percentage modulation is calculated using the following formula:

$$\%\ \text{Modulation} = 100\% \times (\text{mean } RLU \text{ of test sample} - \text{mean } RLU \text{ of } EC20 \text{ control}) / (\text{mean } RLU \text{ of MAX control} - \text{mean } RLU \text{ of } EC20 \text{ control}).$$

4. For Gs antagonist or negative allosteric mode assays, percentage inhibition is calculated using the following formula:

$$\%\ \text{Inhibition} = 100\% \times (1 - \text{mean } RLU \text{ of test sample} - \text{mean } RLU \text{ of vehicle control}) / (\text{mean } RLU \text{ of } EC80 \text{ control} - \text{mean } RLU \text{ of vehicle control})).$$

5. For Gi agonist mode assays, percentage activity is calculated using the following formula:

$$\%\ \text{Activity} = 100\% \times \left(1 - (\text{mean } RLU \text{ of test sample} - \text{mean } RLU \text{ of MAX control}) / (\text{mean } RLU \text{ of vehicle control} - \text{mean } RLU \text{ of MAX control})\right).$$

6. For Gi positive allosteric mode assays, percentage modulation is calculated using the following formula:

$$\%\ \text{Modulation} = 100\% \times \left(1 - (\text{mean } RLU \text{ of test sample} - \text{mean } RLU \text{ of MAX control}) / (\text{mean } RLU \text{ of } EC20 \text{ control} - \text{mean } RLU \text{ of MAX control})\right).$$

7. For Gi inverse agonist mode assays, percentage activity is calculated using the following formula:

$$\%\ \text{Inverse Agonist Activity} = 100\% \times \left((\text{mean } RLU \text{ of test sample} - \text{mean } RLU \text{ of } EC20 \text{ forskolin}) / (\text{mean } RLU \text{ of forskolin positive control} - \text{mean } RLU \text{ of } EC20 \text{ control})\right).$$

8. For Gi antagonist or negative allosteric mode assays, percentage inhibition is calculated using the following formula:

$$\%\ \text{Inhibition} = 100\% \times (\text{mean } RLU \text{ of test sample} - \text{mean } RLU \text{ of } EC80 \text{ control}) / (\text{mean } RLU \text{ of forskolin positive control} - \text{mean } RLU \text{ of } EC80 \text{ control}).$$

The results of the data analysis are summarized in the table below:

| Assay Name | Assay Format | Assay Target | Result Type | RC50 | Unit | Hill | Curve Bottom | Curve Top | Max Response |
|---|---|---|---|---|---|---|---|---|---|
| cAMP | Agonist | OPRM1 | EC50 | 96.60954 | uM | 1.4264 | 1.9045 | 40 | 36.935 |
| cAMP | Antagonist | OPRM1 | IC50 | >300 | uM | | | | 2.1171 |

Figure 6:
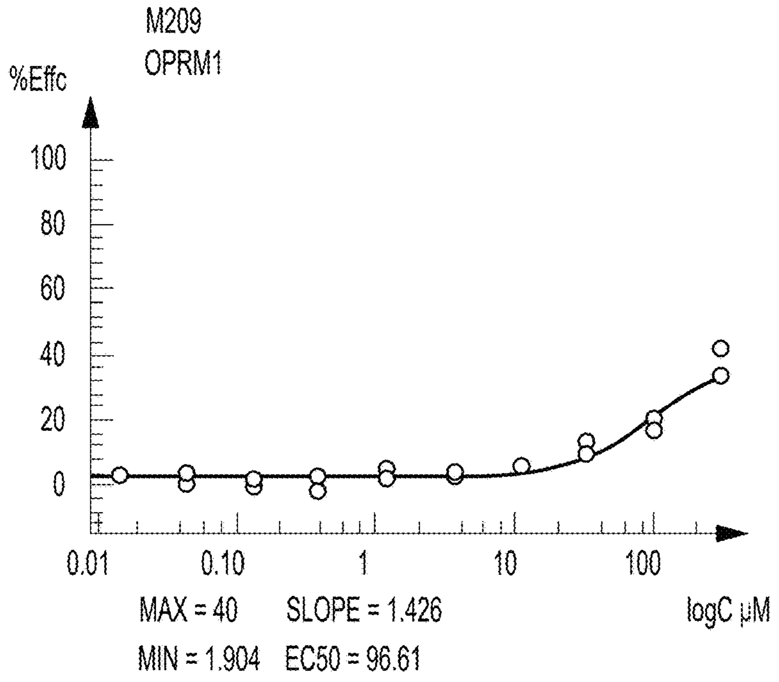
FIG. 6 shows the agonist mode results with the GPCR Biosensor Assay for 2-(2-chlorophenyl)-2-(methylamino) cyclopentan-1-one.
Figure 7:
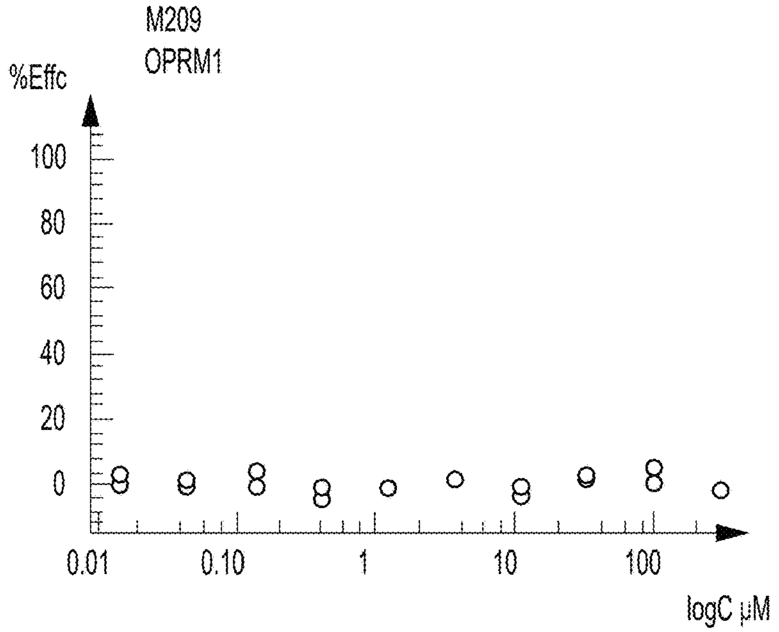
FIG. 7 shows the antagonist mode results with the GPCR Biosensor Assay for 2-(2-chlorophenyl)-2-(methylamino) cyclopentan-1-one.

FIGS. 6 and 7 shows the results for the agonist and antagonist assays, respectively. For the agonist assay, data was normalized to the maximal and minimal response observed in the presence of control ligand and vehicle.

Example 3

This example illustrates a four-step synthesis of 2-(2-chlorophenyl)-2-(methylamino) cyclopentan-1-one pamoate ("M209 pamoate"). The salt may be referred to as "hemi-pamoate" by stoichiometry; however, it is often called "pamoate" to indicate the salt form.

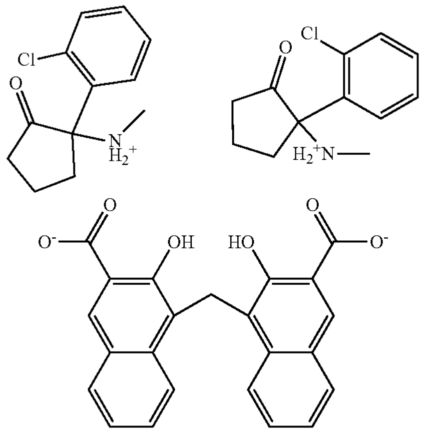

M209 hemipamoate

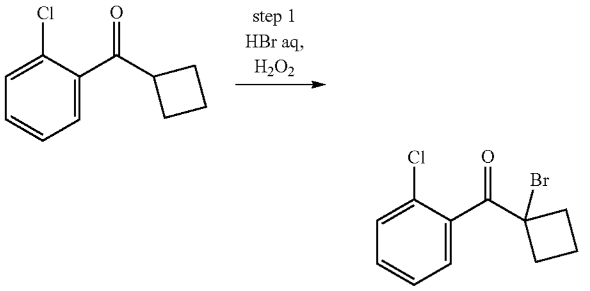

The starting material ("SM") (2-chlorophenyl)-cyclobutyl-methanone (300 g, 1.54 mol, 1 eq) was introduced into a 6 L double jacket reactor. HBr 48% aqueous solution (250 mL, 372 g, 2.21 mol, 1.43 eq) was added and the obtained reaction mixture was cooled to 0-5° C. Then, $H_2O_2$ 30% aqueous solution (359 mL, 394.9 g, 3.48 mol, 2.3 eq) was added dropwise (exothermic reaction). The temperature of the reaction mixture during the addition ranges between 45-55° C. After completion of the addition, the reaction mixture was allowed to cool to room temperature and stirred for 0.5 hours. Since the starting material was still detected in the reaction mixture, the stirring was continued at 55° C. for an additional hour, then, a conversion of about 95% was observed. The reaction mixture was cooled to room temperature and water (1.68 L) was added, followed by hexane (1.68 L). The phases were separated and the organic phase was washed with brine (2.1 L) and 2% $NaHSO_3$ (aq) (1.4 L), dried over $Na_2SO_4$ (400 g), filtered through a glass filter and evaporated to dryness to afford an oily yellow crude (391 g, 93% yield) with 94.69% HPLC purity. The HPLC chromatogram for the intermediate ("Int-1") is provided in FIG. 8.

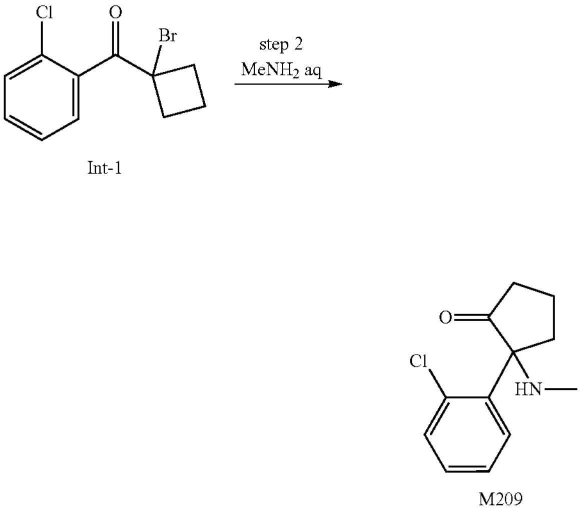

| Material | Amount | Grade | Manufacturer | Cat. no. |
|---|---|---|---|---|
| (2-Chlorophenyl)-cyclobutyl-methanone | 300 g | | Accela | SY342670 |
| Hydrobromic acid, 48% solution in water (HBr) | 250 mL | ACS | Thermo Scientific | 42378 |
| Hydrogen peroxide 30% ($H_2O_2$) | 359 mL | ACS | Fischer chemical | H325 |
| Hexane | 1.68 L | AR | BioLab | 000829052100 |
| Sodium chloride (NaCl) | 546 g | AR | BioLab | 001903059100 |
| Sodium hydrogen sulfite ($NaHSO_3$) | 28 g | ACS | Sigma | 243973 |
| Sodium sulfate ($Na_2SO_4$) | 400 g | AR | BioLab | 001948059100 |
| Water ($H_2O$) | 1.68 L | HPLC | MilliQ system | |

| Material | Amount | Grade | Manufacturer | Cat.no. | Batch/Lot. No. |
|---|---|---|---|---|---|
| Int-1 | 390 g | | Recipharm | | MIR005-AS040 |
| Ethanol (EtOH) absolute | 3.9 L | AR | BioLab | 000525052100 | |
| M209 | 0.1 g | | Recipharm | | MIR003-AS034 |
| Methylamine 40% solution in water ($MeNH_2$) | 3.23 L | Extra pure | Thermo Scientific | 12623 | |
| Water ($H_2O$) | 5 L | HPLC | MilliQ system | | |

In a 6 L double jacket reactor Int-1 (390 g, 1.43 mol, 1 eq) was suspended in methylamine 40% solution in water (3.23 L, 2.9 kg, 37.42 mol, 26 eq). The obtained reaction mixture was heated to 45° C. and stirred vigorously for 1 hour, during which an off-white precipitate was formed. No starting material was detected after 1 hour of stirring. The reaction mixture was cooled to 0-5° C. and stirred at this temperature for an additional 0.5 hour. Then, the precipitate was filtered and washed with water (5 L), until the water filtrate reached pH≤9. The obtained off-white wet product (232 g, 99.1% HPLC purity, 0.58% di-chloro impurity) was forwarded to purification steps.

Figure 11:
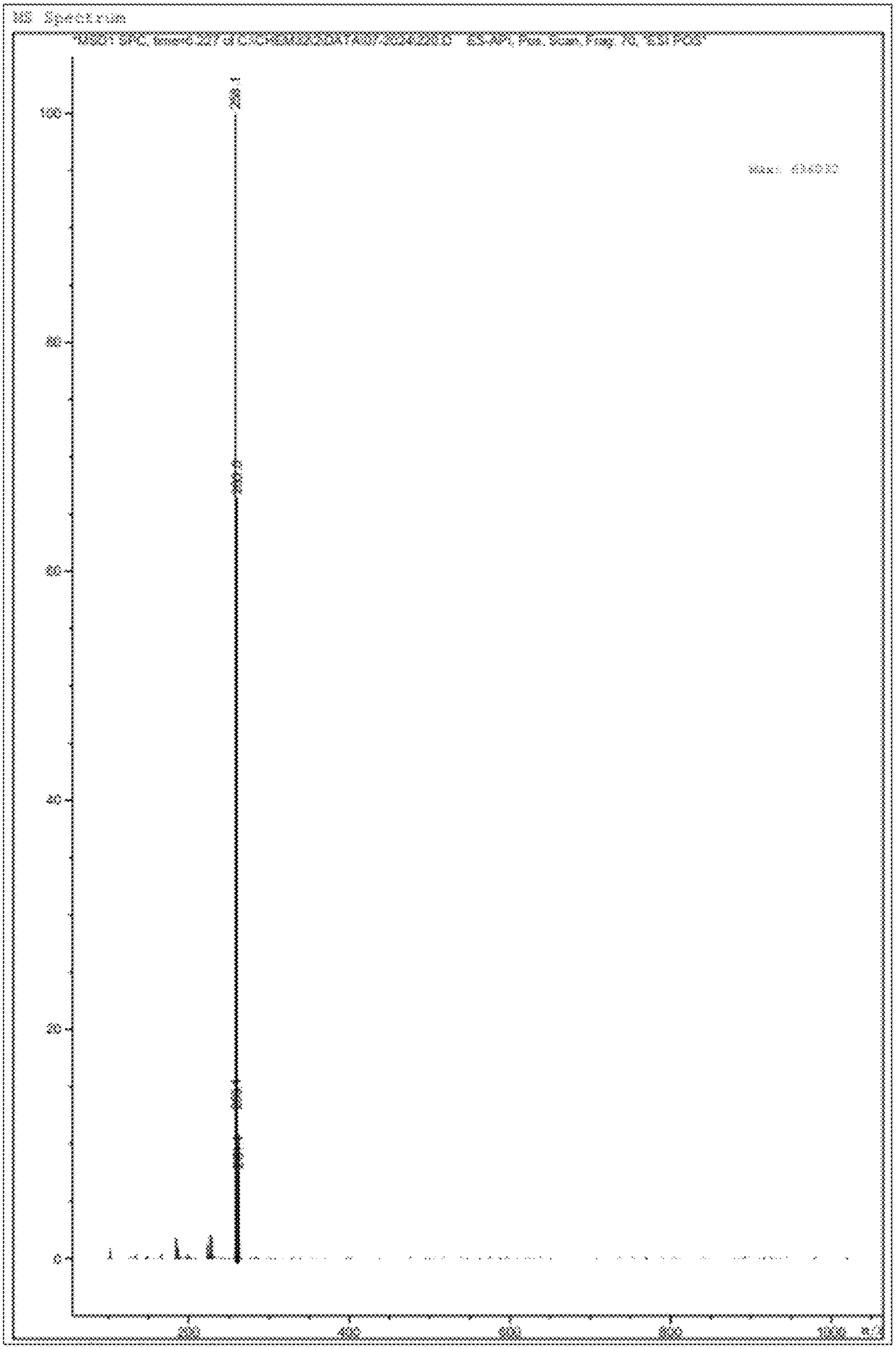
FIG. 11 shows mass spectroscopy analysis of 2-(2-chlorophenyl)-2-(methylamino) cyclopentan-1-one.
Figure 12:
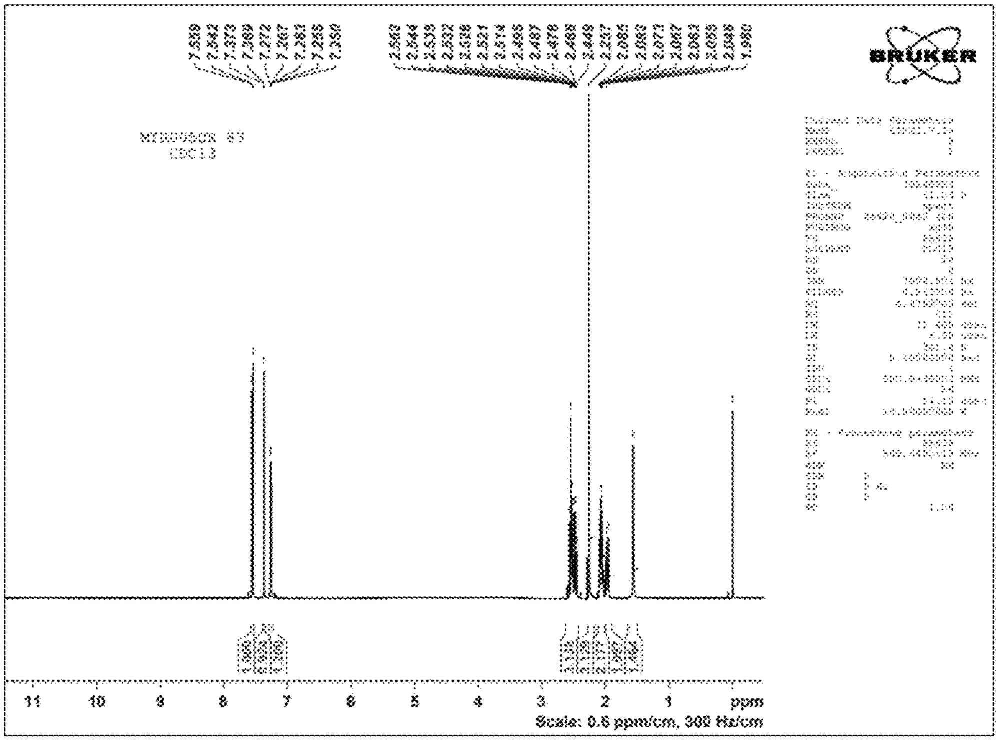
FIG. 12 shows 1H-NMR analysis of 2-(2-chlorophenyl)-2-(methylamino) cyclopentan-1-one.
Figure 13:
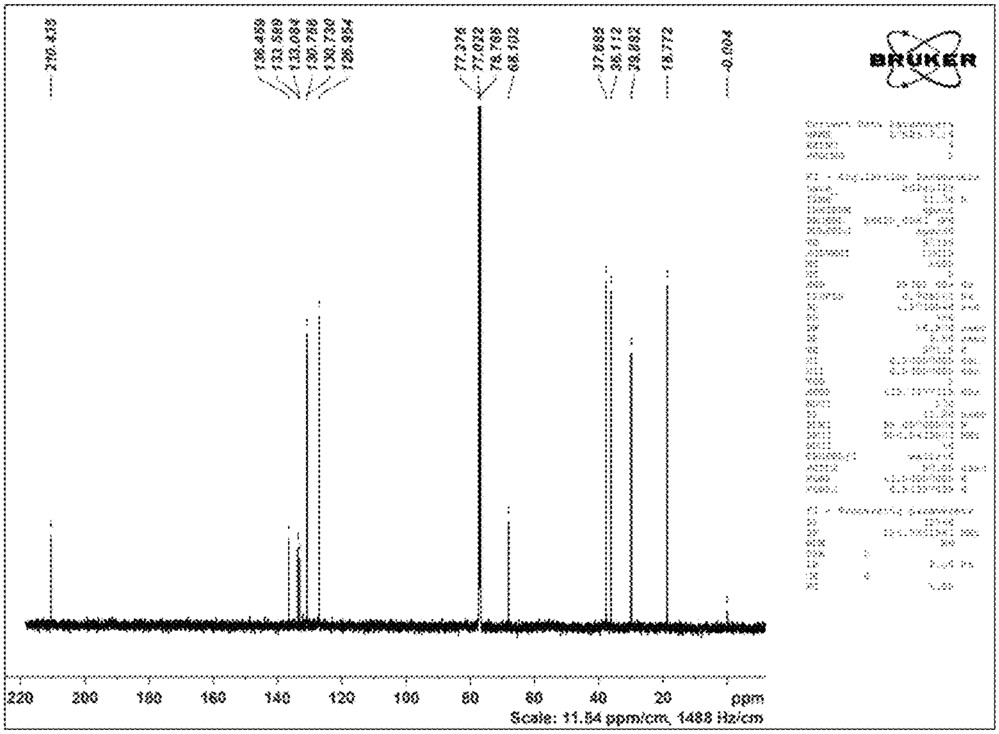
FIG. 13 shows 13C-NMR analysis of 2-(2-chlorophenyl)-2-(methylamino) cyclopentan-1-one.

Recrystallization. Into a 25 L reactor, the previously isolated M209 (232 g) and EtOH (3.5 L) were introduced, and the obtained suspension was heated to 70° C. until full dissolution. When a clear solution was obtained, the reaction mixture was brought to 38° C., and about 0.1 g of seeds of M209 was introduced. Crystallization started and the reaction mixture was gradually cooled to 5° C. during 2 hours and stirred at this temperature for an additional 1 hour. Then, the precipitate was filtered, washed with a pre-cooled to −20° C. EtOH (400 mL), and dried at room temperature in a vacuum oven (8 mbar) until constant weight (187.9 g, 81% yield) to give a white solid with 99.42% HPLC purity (0.43% di-chloro impurity). The HPLC chromatograms for M209 before and after recrystallization are provided in FIGS. 9 and 10, respectively. The MS spectrum, 1H-NMR (500 MHz, $CDCl_3$) and 13C-NMR (126 MHz, $CDCl_3$) for recrystallized M209 are provided in FIGS. 11-13, respectively.

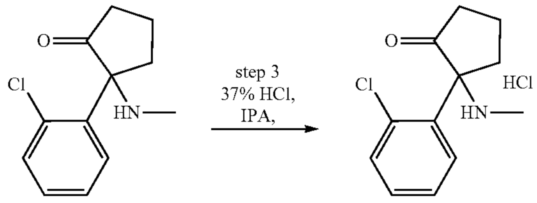

M209 M209 HCl

| Material | Amount | Grade | Manufacturer | Cat. no. | Batch/Lot. No. |
|---|---|---|---|---|---|
| M209 | 187.9 g | | Recipharm | | MIR005-AS042 |
| Hydrochloric acid 37% solution in water (HCl) | 74 mL | AR | BioLab | 000841050100 | |
| Isopropanol (IPA) | 3.5 L | AR | BioLab | 001626050200 | |

In a 4 L one-neck flask the previously isolated M209 (187.9 g, 0.73 mol, 1 eq) was suspended in IPA (2.5 L, 13.3 mL/g), then 37% HCl (74 mL, 87.3 g, 0.89 mol, 1.2 eq) was added and the obtained reaction mixture was heated to 40-45° C. When a clear solution was obtained the solvent was evaporated to dryness under reduced pressure to provide a white wet solid. IPA (1 L) was added and the solvent was evaporated to dryness to provide M209 hydrochloride as a white solid (219 g, 100% yield) with 99.61% HPLC purity (0.35% di-chloro impurity). The HPLC chromatogram for M209 HCl is provided in FIG. 14.

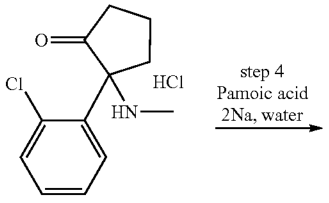

M209 HCl

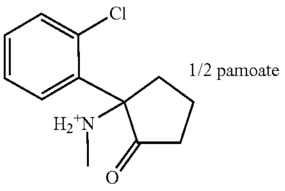

M209 pamoate

| Material | Amount | Grade | Manufacturer | Cat. no. | Batch/Lot. No. |
|---|---|---|---|---|---|
| M209 Hydrochloride | 219 g | | Recipharm | | MIR005-AS045 |
| Pamoic acid disodium salt | 170.3 g | >98% | Angene | AG003TJT | AGN24-163157-1 |
| Water ($H_2O$) | 7 L | HPLC | MilliQ system | | |

Figure 15:
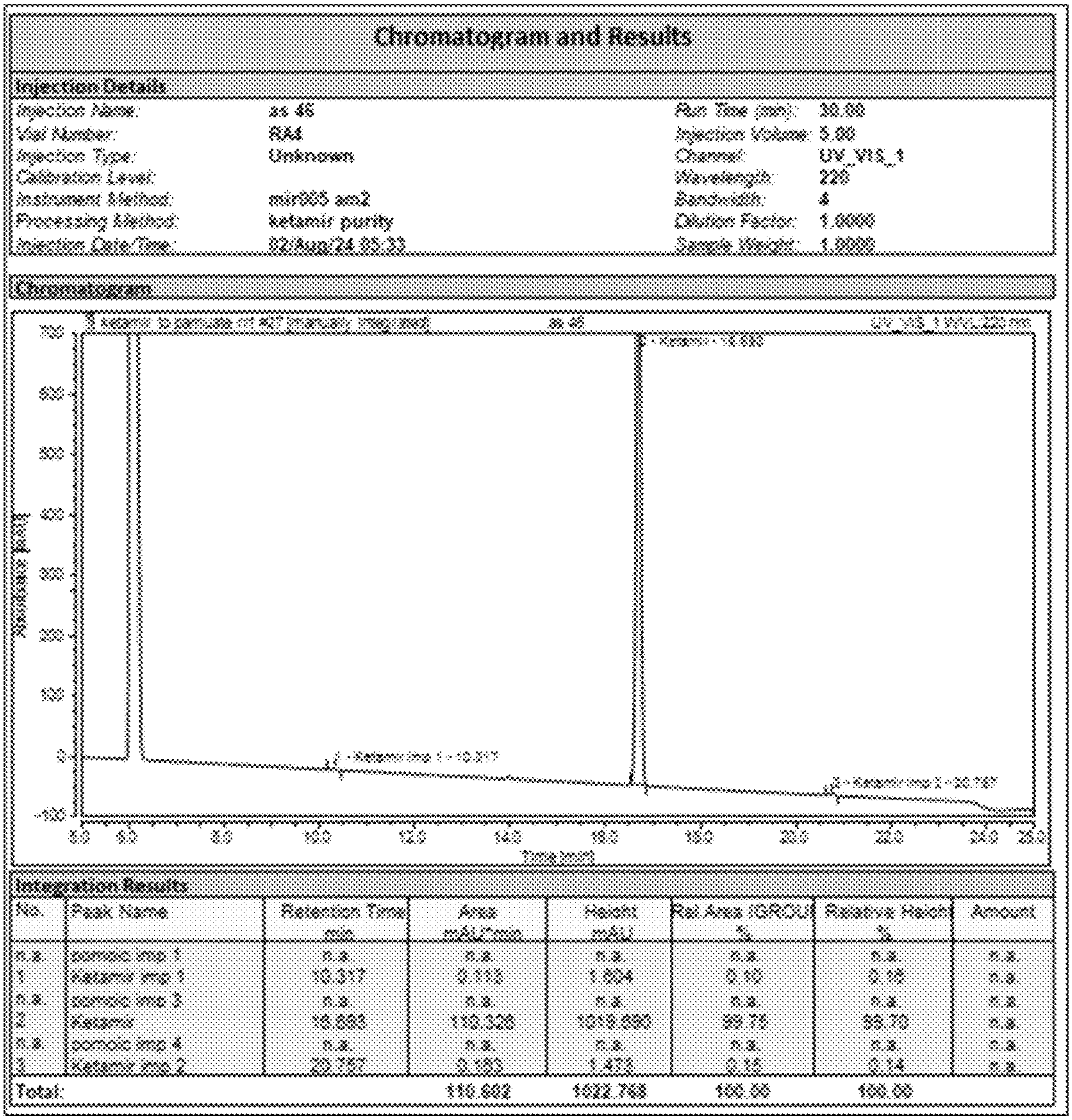
FIG. 15 shows HPLC analysis of the product 2-(2-chlorophenyl)-2-(methylamino) cyclopentan-1-one hemipamoate.
Figure 16:
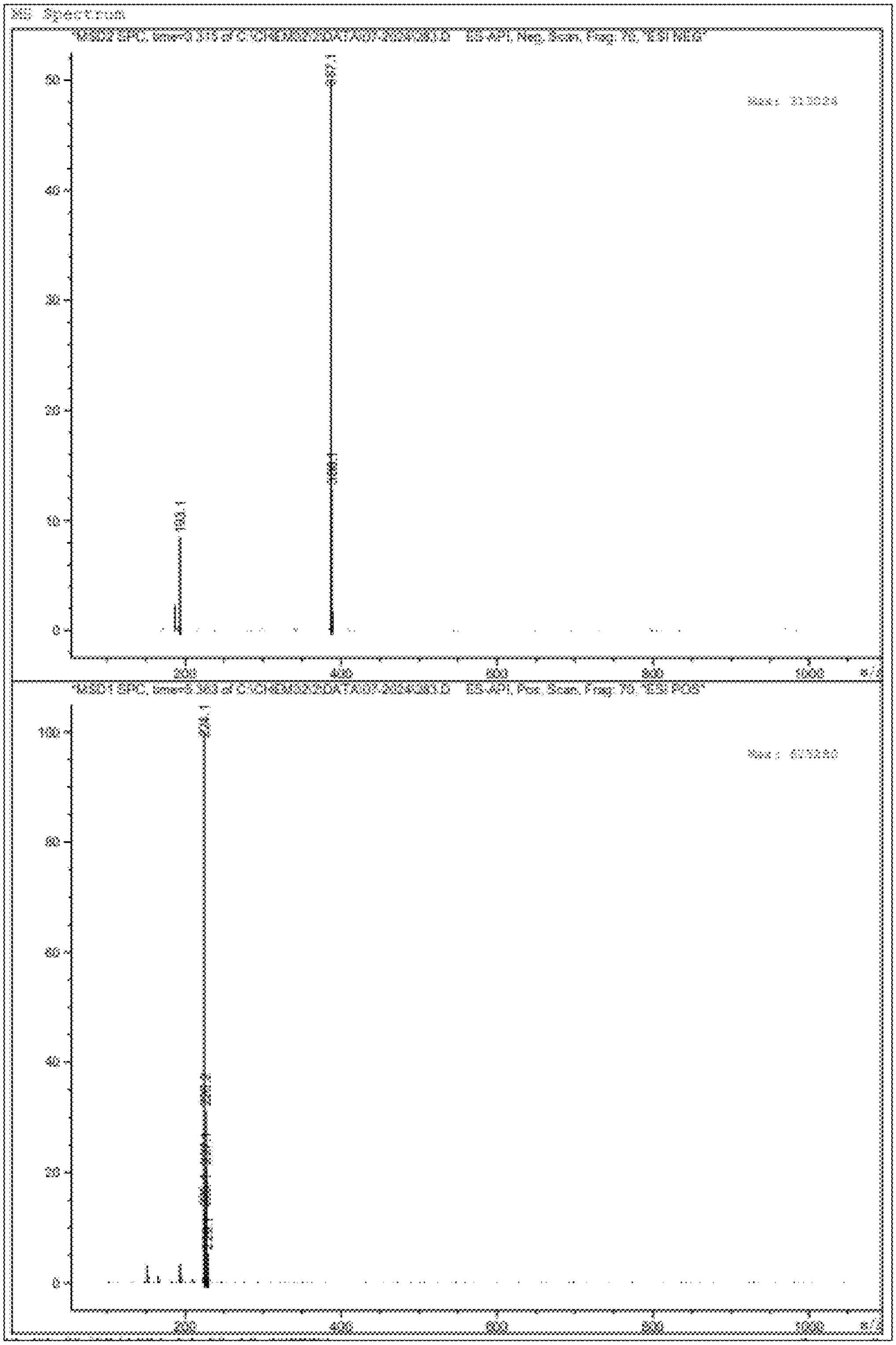
FIG. 16 shows mass spectroscopy analysis of the product 2-(2-chlorophenyl)-2-(methylamino)cyclopentan-1-one hemipamoate.
Figure 17:
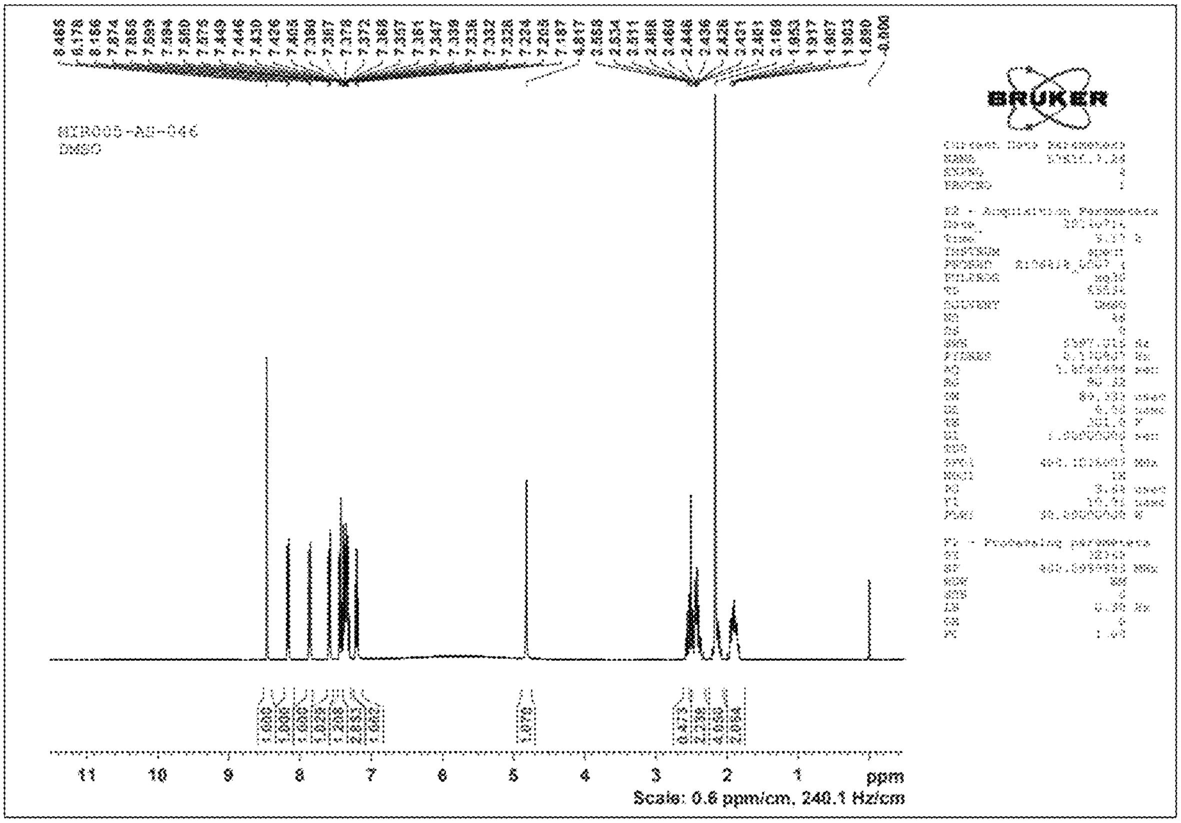
FIG. 17 shows 1H-NMR analysis of the product 2-(2-chlorophenyl)-2-(methylamino) cyclopentan-1-one hemipamoate.

In a 6 L reactor, the previously isolated M209 hydrochloride (batch MIR005-AS045, 219 g, 0.84 mol, 1 eq) was dissolved in water (3.3 L) and stirred at 240 rpm. A solution of a pamoic acid disodium salt (170.3 g, 0.39 mol, 0.47 eq) in water (1.7 L) was prepared in a separate vessel, filtered through a glass filter, transferred into a dropping funnel, and added slowly into the 6 L reactor (with M209 hydrochloride solution inside) during 20 minutes at room temperature. Immediate precipitation was observed. The obtained suspension was stirred for an additional 1 hour and then filtered. The precipitate was washed with water (2 L) and dried at 45° C. in a vacuum oven (25 mbar) until constant weight. After 132 hours 305 g (92% yield) of M209 Hemipamoate was obtained as a yellowish solid with a purity of 99.75% (0.15% di-chloro impurity) and 1.166 w/w ratio M209: Pamoate by HPLC Method MIR-AM-001. The HPLC chromatogram for M209 pamoate is provided in FIG. 15. The MS spectrum and 1H-NMR (500 MHz, $CDCl_3$) for M209 pamoate are provided in FIGS. 16 and 17, respectively.

| Monitoring by HPLC-MS | | |
|---|---|---|
| Instrument name | Manufacturer | Model/Cat. No |
| LCMS | Agilent | 1260 Infinity |
| UV detector | Agilent | 1260 DAD |
| MS detector | Agilent | MSD 6120 |

| Materials and reagents | | | |
|---|---|---|---|
| Material | Grade | Manufacturer | Cat. no. |
| Water ($H_2O$) | HPLC | MilliQ | |
| Acetonitrile (ACN) | LCMS | J. T. Baker | 9821 |
| Ammonium hydrogen carbonate | HPLC | Merck | 5.33005.0050 |

Chromatographic System

Column: Waters XBridge C18, 50×3 mm, 3.5 μm, RIS ID: 13-03

Column temperature: 40° C.

Flow rate: 1 mL/min

UV Detection: 220 nm

Mobile Phase A: 10 mM ammonium carbonate in water

Mobile Phase B: acetonitrile

Sample Diluent: acetonitrile:water (1:1)

Injection volume: 2 μL

| Gradient: | | |
|---|---|---|
| Time (min) | Eluent % A | Eluent % B |
| 0.0 | 90 | 10 |
| 1.0 | 90 | 10 |
| 9.0 | 10 | 90 |
| 10.0 | 10 | 90 |
| 10.1 | 90 | 10 |

Ionization: ESI

Capillary voltage: POS: 4000 V, NEG: 3500 V

Drying gas temperature: 350° C.

Drying gas flow: 11.0-12.0 L/min

Nebulizer pressure: 45-60 psig

| Release of M209 Hemipamoate | | |
|---|---|---|
| Instrument name | Manufacturer | Model/Cat. No |
| HPLC | Dionex | Ultimate 3000 |
| UV detector | Dionex | Ultimate 3000 |
| Ultrasonic bath | MRC | |
| Multi stirrer plate | IKA | RO5 |
| Vortex mixer | | |
| Analytical balance | Sartorius | Cubis |

| Ingredient (% w/w) | Lot A | Lot B | Lot C |
|---|---|---|---|
| M209 pamoate | 5 | 5 | 5 |
| White petrolatum | 77 | 84 | 85 |
| DMSO | 10 | 5 | 0 |
| GMS SE | 3 | 1 | 0 |
| Mineral oil | 5 | 5 | 10 |
| Total | 100 | 100 | 100 |

| Materials and reagents | | | |
|---|---|---|---|
| Material | Grade | Manufacturer | Cat.no. |
| Acetonitrile (ACN) | HPLC | BioLab | 000120350200 |
| Ammonium acetate | HPLC | Sigma | 73594 |
| Ammonium hydroxide 28-30% | HPLC | J. T. Baker | 9721-01 |
| Water ($H_2O$) | HPLC | MilliQ | |

Chromatographic System

- Column: YMC-Triart C18 150×4.6 mm, S-3 μm Cat: YMTA12S03-1546PTH
- Column temperature: 40° C.
- Mobile phase A: ammonium acetate pH=8.5
- Mobile phase B: acetonitrile
- Flow rate: 1 mL/min
- UV Detector: 220±2
- Autosampler temperature: Ambient
- Injection volume: 5 μL
- Diluent: 20 mmol ammonium acetate in water (pH 8.5)/acetonitrile; 7/3, v/v

| Gradient: | | |
|---|---|---|
| Time, min | Eluent % A | Eluent % B |
| 0.0 | 80 | 20 |
| 2.0 | 80 | 20 |
| 22.0 | 30 | 70 |
| 22.3 | 20 | 80 |
| 24.8 | 20 | 80 |
| 25.0 | 80 | 20 |
| 30.0 | 80 | 20 |

M209 pamoate is a yellowish to light yellow solid that is freely soluble in dimethyl sulfoxide (DMSO) and ethanol. The API is packed in a medical grade LDPE bag and stored at a room temperature 25±2° C. The enantiomeric purity of M209 was studied by optical rotation of M209 pamoate. It was found an optical rotation values of [0] for M209, suggesting that all tested samples contain the equal amounts of "S" and "R" enantiomers, resulting in no optical activity of the drug substance. Its molecular weight is 835.77 g/mol.

Example 4

This example illustrates preparing a topical ointment containing 5% (w/w) of 2-(2-chlorophenyl)-2-(methylamino)cyclopentan-1-one pamoate ("M209 pamoate") from Example 2. Three lots of the ointment were prepared having the following compositions.

Lots A and B

1. In a separate beaker, M209 hemipamoate was dissolved in DMSO. Mineral oil was added. After thorough mixing, the mixture was heated to 70° C.
2. In a main beaker, white petrolatum and GMS SE were mixed and heated to 70° C. until a clear phase was observed.
3. The materials from steps 1 and 2 were combined throughout homogenization. Mixing was continued with cooling down. The resulting ointment was packed in 10 g aluminum tubes at 45-50° C.

Lot C

1. In a separate beaker, M209 hemipamoate was dispersed in mineral oil, mixed well and heated to 70° C.
2. In a main beaker, white petrolatum and GMS SE were mixed and heated to 70° C. until a clear phase was observed.
3. The materials from steps 1 and 2 were combined throughout homogenization. Mixing was continued with cooling down. The resulting ointment was packed in 10 g aluminum tubes at 45-50° C.

While the invention has been described with respect to specific examples, those skilled in the art will appreciate that there are numerous variations and permutations of the above described systems and techniques that fall within the spirit and scope of the invention as set forth in the appended claims.

What is claimed is:

1. A compound having a structure of Formula (I):

Formula (I)

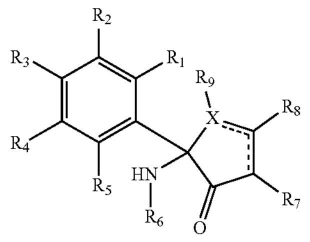

wherein $R_1$, $R_2$, $R_3$, $R_4$ and $R_5$ are each independently H or a halogen, $R_6$ is $C_{1-3}$ alkyl, $R_7$ is H or OH, $R_8$ is H or $C_{1-3}$ alkyl, and $R_9$ is H, an electron pair or OH;

wherein ---- is a single bond or a double bond with the proviso that at least one ---- is a single bond; wherein at least one of $R_1$, $R_2$, $R_3$, $R_4$, and $R_5$ is a halogen; and wherein X is C or N;

or a pharmaceutically acceptable salt or ester thereof.

2. The compound of claim 1, wherein $R_1$ is selected from the group consisting of fluorine (F), chlorine (Cl), bromine (Br), and iodine (I).

3. The compound of claim 2, wherein $R_1$ is Cl.

4. The compound of claim 1, wherein $R_6$ is methyl.

5. The compound of claim 1, wherein both ---- are single bonds.

6. The compound of claim 1, wherein the compound has a structure according to Formula (II):

Formula (II)

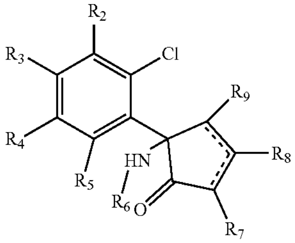

or a pharmaceutically acceptable salt or ester thereof.

7. The compound of claim 1, wherein X is N.

8. The compound of claim 1 having a structure selected from the group consisting of:

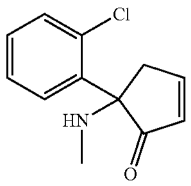

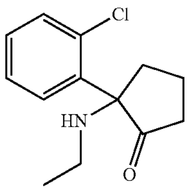

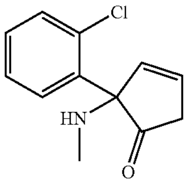

and

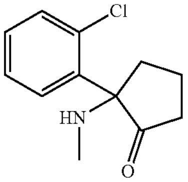

or a pharmaceutically acceptable salt or ester thereof.

9. The compound of claim 1 having a structure selected from the group consisting of:

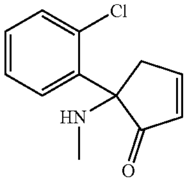

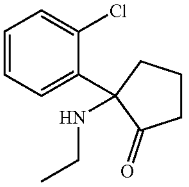

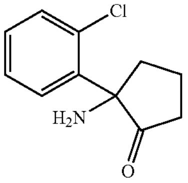

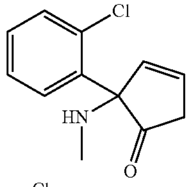

and

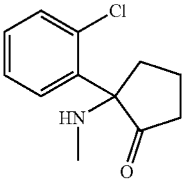

, or a pharmaceutically acceptable salt or ester thereof.

10. A pharmaceutical composition comprising an effective amount of the compound of claim 1 and a pharmaceutically acceptable vehicle therefor.

11. A method of treating depression, anxiety, asthma, or pain comprising administering to an individual in need thereof the pharmaceutical composition of claim 10.

12. A method of inducing anesthesia or sedation comprising administering to an individual in need thereof the pharmaceutical composition of claim 10.

13. The compound of claim 1 which is 2-(2-chlorophenyl)-2-(methylamino) cyclopentan-1-one or a pharmaceutically acceptable salt thereof.

14. The compound of claim 10 which is 2-(2-chlorophenyl)-2-(methylamino) cyclopentan-1-one hemipamoate.

15. A pharmaceutical composition comprising an effective amount of the compound of claim 13 and a pharmaceutically acceptable vehicle therefor.

16. The pharmaceutical composition of claim 15 which is formulated as an ointment for topical administration.

17. A method of treating a disorder selected from the group consisting of depression, anxiety, asthma, and pain, the method comprising administering to an individual in need thereof the pharmaceutical composition of claim 15.

18. The method claim 17, wherein the disorder is depression.

19. The method claim 17, wherein the disorder is anxiety.

20. The method claim 17, wherein the disorder is pain.

* * * * *